US010888675B2

(12) United States Patent
Holakovsky et al.

(10) Patent No.: US 10,888,675 B2
(45) Date of Patent: Jan. 12, 2021

(54) INHALER

(71) Applicant: Boehringer Ingelheim International GmbH, Ingelheim am Rhein (DE)

(72) Inventors: Holger Holakovsky, Schöneberg (DE); Jens Besseler, Bingen am Rhein (DE); Jessica Frentzel-Beyme, Gau-Algesheim (DE); Frank Herrmann, Duisburg (DE); Markus Kaemper, Breckerfeld (DE)

(73) Assignee: Boehringer Ingelheim International GmbH

( * ) Notice: Subject to any disclaimer, the term of this patent is extended or adjusted under 35 U.S.C. 154(b) by 201 days.

(21) Appl. No.: 16/076,887

(22) PCT Filed: Feb. 22, 2017

(86) PCT No.: PCT/EP2017/025032
§ 371 (c)(1),
(2) Date: Aug. 9, 2018

(87) PCT Pub. No.: WO2017/144182
PCT Pub. Date: Aug. 31, 2017

(65) Prior Publication Data
US 2019/0091422 A1    Mar. 28, 2019

(30) Foreign Application Priority Data

Feb. 24, 2016    (EP) .................................... 16020052

(51) Int. Cl.
*A61M 15/00*    (2006.01)
(52) U.S. Cl.
CPC ........ *A61M 15/003* (2014.02); *A61M 15/005* (2014.02); *A61M 15/0026* (2014.02);
(Continued)

(58) Field of Classification Search
CPC .......... A61M 15/0026; A61M 15/0025; A61M 15/0021; A61M 15/0063; A61M 15/003;
(Continued)

(56) References Cited

U.S. PATENT DOCUMENTS 4,889,114 A * 12/1989 Kladders ........... A61M 15/0041
128/203.15
5,595,175 A *  1/1997 Malcher ............ A61M 15/0028
128/203.15
(Continued)

FOREIGN PATENT DOCUMENTS

CN    204521855 U    8/2015
CN    204890849 U    12/2015
(Continued)

OTHER PUBLICATIONS

English abstract for CN204521855, Mar. 13, 2015.
(Continued)

*Primary Examiner* — Kendra D Carter
*Assistant Examiner* — Eric Theisen
(74) *Attorney, Agent, or Firm* — Matthew B. Dernier, Esq.

(57) ABSTRACT

An inhaler including a magazine having capsules, a mouthpiece and a cover associated with the mouthpiece, where the cover is radially movable and pivotable for open or closing of the mouthpiece, by pivoting the cover the magazine is conveyed from one capsule to the next capsule, and by radial movement of the cover a capsule is moved in a radial direction into a discharge position.

15 Claims, 22 Drawing Sheets

(52) U.S. Cl.
CPC .... *A61M 15/0035* (2014.02); *A61M 15/0041* (2014.02); *A61M 2202/064* (2013.01)

(58) Field of Classification Search
CPC .......... A61M 15/0031; A61M 15/0033; A61M 15/0035; A61M 15/0036; A61M 15/0038; A61M 15/004; A61M 15/0041; A61M 15/0043
See application file for complete search history.

(56) References Cited

U.S. PATENT DOCUMENTS

| | | | | |
|---|---|---|---|---|
| 8,298,575 | B2 * | 10/2012 | Hochrainer | A61K 9/4816 424/454 |
| 8,584,669 | B2 * | 11/2013 | Besseler | A61M 15/0028 128/200.11 |
| 8,584,673 | B2 | 11/2013 | Thoemmes | |
| 8,746,244 | B2 * | 6/2014 | Kaemper | A61M 15/0061 128/203.21 |
| 9,956,361 | B2 | 5/2018 | Von Schuckmann | A61M 15/005 |
| 2001/0008637 | A1 * | 7/2001 | Hochrainer | A61K 9/4816 424/451 |
| 2004/0131668 | A1 * | 7/2004 | Hochrainer | A61M 15/0028 424/451 |
| 2005/0178382 | A1 * | 8/2005 | Riley | A61M 15/0025 128/203.15 |
| 2007/0131225 | A1 * | 6/2007 | Rand | A61M 15/0028 128/200.23 |
| 2008/0295834 | A1 | 12/2008 | Thoemmes | |
| 2010/0065048 | A1 * | 3/2010 | Mueller-Walz | A61M 15/0026 128/203.15 |
| 2010/0294278 | A1 * | 11/2010 | Mosier | A61M 15/0041 128/203.14 |
| 2011/0232637 | A1 | 9/2011 | Kaemper | |

FOREIGN PATENT DOCUMENTS

| | | |
|---|---|---|
| CN | 204890850 U | 12/2015 |
| EP | 0147755 A2 | 7/1985 |
| EP | 0528764 A1 | 2/1993 |
| JP | H09262295 A | 10/1997 |
| JP | 2010528693 A | 8/2010 |
| WO | 0007572 A2 | 2/2000 |
| WO | 2005049121 A1 | 6/2005 |
| WO | 2005089842 A1 | 9/2005 |
| WO | 2007118648 A1 | 10/2007 |
| WO | 2008145348 A2 | 12/2008 |
| WO | 2011073306 A1 | 6/2011 |
| WO | 2011039307 A2 | 7/2011 |
| WO | 2013150021 A1 | 10/2013 |

OTHER PUBLICATIONS

English abstract for CN204890849, Dec. 23, 2015.
English abstract for CN204890850, Dec. 23, 2015.
English abstract for JPH09262295, Oct. 7, 1997.
English abstract for WO2005089842, Sep. 29, 2005.
International Search Report for corresponding application PCT/EP2017/025032, dated Jul. 27, 2017.

* cited by examiner

INHALER

BACKGROUND

The present invention relates in particular to an inhaler for discharge or inhalation of a formulation which is preferably in powder form, i.e. a powder inhaler.

The formulation is in particular a therapeutic agent or pharmaceutical preparation. Accordingly, in particular, the formulation contains at least one active substance or consists thereof. Thus the formulation serves in particular for medical treatment or other therapeutic purposes.

In the present invention, the formulation is held in capsules, wherein each capsule contains one dose of the formulation. Thus the formulation is pre-dosed into the capsules.

In the present invention, the term "capsule" should be understood primarily to mean containers having a solid or an at least substantially rigid, in particular dense, integral, closed and/or continuous shell, which in particular can be manipulated and/or opened separately from one another.

Preferably, in a further sense according to the present invention, the term "capsule" should also be understood to mean other containers, packages or the like with a dose of the formulation in each case, which in particular can be manipulated and/or opened separately from one another.

EP 0 147 755 A2 discloses an inhaler for the inhalation of pharmaceutical preparations in powder form from elongated capsules. The inhaler has a capsule chamber, into which a capsule can be introduced manually in each case. The capsule is pierced lengthwise and thereby opened by manual actuation of an opening device in the capsule chamber. During inhalation, an air stream flowing through the capsule chamber leads to the capsule being moved to and fro in the capsule chamber, wherein the pharmaceutical preparation in powder form is discharged and dispersed in the air stream. The present invention uses this principle in particular, but it can also be used in other techniques for discharging a formulation.

WO 2005/049121 A1 discloses a powder inhaler having a plurality of capsules. The cylindrical capsules are guided upright one behind the other by a rail or are connected to one another in the manner of a chain.

WO 2007/118648 A1 discloses a powder inhaler, which has in particular a plurality of capsule chambers with capsules held therein, wherein each capsule chamber is in particular used only once. The capsules and capsule chambers can be oriented radially, wherein the outlet openings of the capsule chambers can be covered by a common cover. In this case, the capsules and capsule chambers can also be arranged in two axially offset planes. According to another embodiment, the inhaler can also have only one capsule chamber for holding individual capsules successively to be emptied during inhalation. Furthermore, during pivoting a mouthpiece cover can move the capsules forwards and individually into the capsule chambers.

WO 2011/039307 A2 discloses an inhaler for the inhalation of pharmaceutical preparations in powder form from capsules, the inhaler having a replaceable tube which forms a capsule chamber having an adjoining dispensing channel, wherein a capsule has been previously inserted into the capsule chamber. The replaceable tube has openings for needles for piercing the respective capsule, wherein the openings can be closed automatically by a membrane.

US 2010/0294278 A1 discloses a powder inhaler having a rotatable blister pack. Blisters which in each case contain a dose of a powdered medicament are arranged radially in the blister pack. The blister pack can be rotated for actuation of a lever. The blisters can be individually moved radially into a discharge position, in which the blister is opened and then the medicament can be inhaled by the patient.

SUMMARY

A capsule chamber in the sense of the present invention is preferably an at least substantially rigid or firm and/or elongated container or capsule housing having an in particular elongated or cylindrical chamber, in which the respective capsule is in particular movable to and fro for emptying or can be moved in another manner or can be made to vibrate or to oscillate. In particular the capsule chamber has an inlet and outlet preferably at opposite ends, so that air can flow through the chamber in order to set the capsule in motion or vibration and/or to discharge the formulation from the capsule.

The object of the present invention is to provide an inhaler which allows simple handling and/or a simple or compact design.

The above object is achieved by an inhaler according to claim 1 or claim 5. Advantageous developments are the subject matter of the subordinate claims.

According to one aspect of the present invention, a cover associated with the mouthpiece of the inhaler is both radially movable and also pivotable, so that by pivoting of the cover the magazine is conveyed or rotated from one capsule to the next capsule, and by radial movement of the cover a capsule is moved or conveyed, in particular pushed, radially into a discharge position. This allows very simple handling with a compact construction, even if a number of capsules are received in the inhaler.

In particular, different mechanisms can thus be triggered by different movements of the cover. Preferably by pivoting of the cover in one direction and/or in both directions, the magazine can transported or moved further or rotated. A capsule or capsule chamber can be moved into a discharge position preferably by radial movement or pulling of the cover outwards. In particular by an opposing movement or closing movement of the cover the used capsule or capsule chamber can be moved or pushed back again—preferably automatically or by spring force—into a storage position or starting position.

In the context of the present invention, the term "radial", "radial movement" or "radial direction" is preferably understood to mean a direction or movement in a direction from the inside to the outside or vice versa, in particular along a radius or diameter of a component which is at least substantially circular, plate-shaped and/or disc-shaped, particularly preferably a housing or magazine of the inhaler. The radial movement or a radial shifting of the cover should preferably be understood as a relative movement of the cover to the housing, magazine and/or mouthpiece of the inhaler along a radius or diameter or from the inside to the outside or vice versa.

The mouthpiece of the inhaler is preferably arranged in a radial edge region of the inhaler or externally. In particular, the magazine having the capsules is arranged radially further inwards than the mouthpiece, preferably in such a way that the capsules are moved by a radial movement from the magazine towards the mouthpiece or from the inside to the outside and/or from the outside to the inside or to the magazine.

In particular by a radial movement of the cover from the inside to the outside or from a centre of the inhaler to the mouthpiece, a capsule is moved out of the magazine or radially or from the inside to the outside or in the direction of the mouthpiece.

In particular by a radial movement of the cover from the outside to the inside or from the mouthpiece to a centre of the inhaler, the capsule used is moved radially or from the outside to the inside or in the direction of a centre of the inhaler or (back) to the magazine.

The term "pivoting" or "pivoting movement" should preferably be understood to mean a movement on a circular path. In particular, the cover or the arms thereof is/are pivotably connected to the housing or mounted thereon or therein, preferably in a centre of the inhaler, in particular in such a way that the cover or the outer end thereof is pivotable. In particular by pivoting of the cover, the mouthpiece can be freed or covered as required.

The cover is preferably both radially movable and also pivotable, wherein the cover is then pivotable by a radial movement outwards and/or is then rotationally fixed or secured in its rotary position by a radial movement inwards. In particular, the cover is not simultaneously radially movable and pivotable, or for the pivoting movement a preceding radial movement outwards is necessary.

According to a further aspect of the present invention, which can also be implemented independently, the capsule chambers are preferably radially movably received in a magazine and can be moved individually radially into a discharge position. This is again conducive to a simple and compact structure, in particular when the inhaler or the magazine thereof holds a plurality of capsules and capsule chambers, which in each case are used only once.

Particularly preferably, only one capsule is provided per capsule chamber. This is advantageous in particular when sticky or readily agglomerating powders are used.

In principle, however, a capsule chamber even can also be used for a plurality of capsules or a number of times. This makes it possible to increase the number of capsules which can be accommodated in an inhaler or magazine.

According to one embodiment, the capsules are preferably moved without an associated capsule chamber out of the magazine into the common capsule chamber or discharge position. This allows a particularly compact structure of the magazine or inhaler and/or the accommodation of a particularly large number of capsules while the overall size remains the same.

Alternatively, a capsule, preferably together with its associated capsule chamber, is moved radially out of the magazine. This allows more space for the opening or piercing of the respective capsule in the discharge position or capsule chamber than if the capsules in the capsule chambers were opened or pierced directly in the magazine. This facilitates the most compact arrangement possible of a plurality of capsules and capsule chambers in the magazine. Accordingly, a compact structure of the inhaler and of the magazine is possible overall.

The aforementioned aspects as well as the aspects of the present invention which emerge from the further description can be implemented independently of one another, but also in any combination.

BRIEF DESCRIPTION OF THE DRAWING

Individual aspects, features, characteristics and advantages of the present invention emerge from the claims and the following description of preferred embodiments with reference to the drawings. In the drawings:

Figure 1:
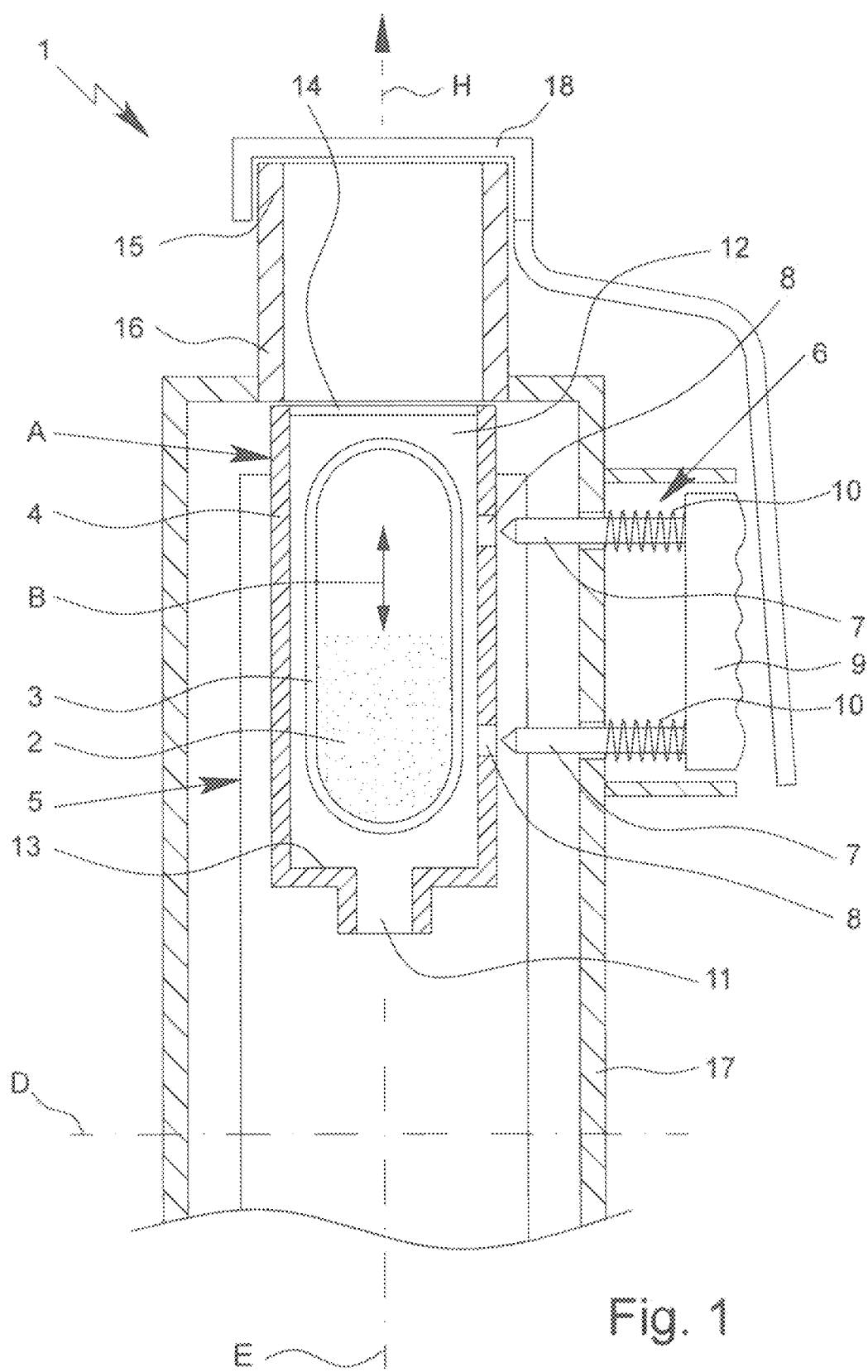
FIG. 1 is a schematic sectional representation of the functional principle of a proposed inhaler.

In the drawings, the same reference signs are used for the same or similar parts, even if a repeated description is omitted. In particular, the same or corresponding advantages and characteristics also emerge. Individual drawings also may not be true to scale for reasons of representation or simplification.

DETAILED DESCRIPTION

FIG. 1 shows in a schematic section the basic structure or the basic functional principle of a proposed inhaler 1. The statements in this connection apply in particular correspondingly and additionally to all the embodiments described later.

The inhaler 1 is preferably designed to be portable and in particular only operates mechanically.

The inhaler 1 serves for discharge or atomisation, in particular for inhalation of the formulation 2 preferably in powder form from capsules 3. Thus the formulation 2 is pre-dosed in doses which are received in the capsules 3. If required, the capsules 3 can also contain different formulations 2.

The formulation 2 is in particular a formulation in the sense mentioned at the outset.

The capsules 3 are in particular capsules in the sense mentioned at the outset.

The inhaler 1 preferably has at least one capsule chamber 4, in particular wherein the capsule chamber 4 is designed to hold an (associated) capsule 3. Particularly preferably, the inhaler 1 has a plurality of capsule chambers 4, in particular one capsule chamber 4 for each capsule 3. However, other solutions are also possible, as is explained in greater detail below.

In the schematic section, a capsule 3 is shown inside a capsule chamber 4 of the inhaler 1. The capsule 3 is still closed, i.e. not yet opened.

The capsule chamber 4 is in particular a capsule chamber in the sense mentioned at the outset.

The capsules 3 are preferably elongated. However, in principle the capsules 3 can have any other suitable shape and can be spherical for example.

In principle, the capsules 3 can be produced from or consist of any suitable material. Gelatine is preferably used as capsule material. In this case, gelatine can be used in a mixture with other additions selected from the group consisting of polyethylene glycol (PEG), preferably PEG 3350, glycerol, sorbitol, propylene glycol, PEO-PPO block copolymers and other polyalcohols and polyethers. Particularly preferably, gelatine is used in the mixture with PEG, preferably PEG 3350. A gelatine capsule 3 particularly preferably contains PEG in a proportion of 1 to 10% (wt. %), preferably 3 to 8%. Particularly preferred gelatine capsules 3 contain PEG in a proportion of 4 to 6%, wherein a PEG proportion of approximately 5% is most preferred. In the case of gelatine-containing capsule materials, the capsules 3 preferably have a Tews or halogen dryer moisture content of less than 12%, particularly preferably of ≤10%.

If cellulose derivatives are used as capsule material, the use of hydropropylmethyl cellulose, hydroxypropyl cellulose, methyl cellulose, hydroxymethyl cellulose and hydroxyethyl cellulose is preferred. In this case, hydropropylmethyl cellulose (HPMC) is particularly preferred, particularly preferably HPMC 2910, as capsule material. In the case where cellulose derivatives are used as capsule materials, the degree of Tews or halogen dryer moisture content is preferably less than 8%, particularly preferably less than 5%. Most preferably, before filling with a tiotropium-containing inhalation powder, inhalation capsules 3 made of cellulose derivatives are dried to a Tews or halogen dryer moisture content of less than 4%, particularly preferably less than 2%.

The capsules 3 can each consist of a capsule body and a capsule cap, as disclosed in particular in WO 00/07572 A2. Therefore reference is hereby made explicitly to the content of WO 00/07572 A2 in its entirety. In this two-part construction, plastics material is used in particular as the capsule material. In particular, the capsule body and the capsule cap consist of the same material. They are connected to one another so that a stable, closed cavity of defined volume is formed. In this case, plastics material, in particular polyethylene, is particularly preferably used.

The capsules 3 can have latching elements which connect the capsule cap firmly to the capsule body.

The capsules 3 and optionally the capsule chambers 4 (if a plurality of capsule chambers 4 are present) are preferably held in a magazine 5 of the inhaler 1. In the schematic section according to FIG. 1, the magazine 5 is only indicated schematically.

The magazine 5 is in particular flat, disc-like or annular. In particular, it has a central or main plane E.

The magazine 5 can optionally be inserted and/or replaced in the inhaler 1 (not shown).

The capsules 3 and optionally the capsule chambers 4 are arranged or received in or on the magazine 5 preferably at least substantially in an annular manner, preferably with an at least substantially radial orientation.

The magazine 5 is preferably movable or rotatable in the inhaler 1, in this case about an axis of rotation D which is preferably perpendicular to the plane E, in particular so that the magazine 5 can be moved or conveyed or (further) rotated from one capsule 3 to the next capsule 3, particularly preferably in order to bring the capsules 3 individually into a discharge position A, as shown by way of example in FIG. 1.

As already mentioned, each capsule 3 preferably contains one dose of the formulation 2. Since the magazine 5 contains a plurality of capsules 3 and a corresponding number of doses, the inhaler 1 can ensure that a user or patient is supplied with the formulation 2, i.e. a medicament or the like, for example for a week or several weeks or even for a month.

The capsules 3 can preferably be opened individually in the inhaler 1. For opening, the inhaler 1 has an opening device 6 which is associated with the capsule chamber 4 or the capsule 3 or the discharge position A. If required, a plurality of opening devices 6 can be provided which are in each case associated with a capsule chamber 4 or capsule 3. Preferably, however, only one common opening device 6 is provided.

The opening of the capsule 3 preferably takes place in each case by piercing. For this purpose, the opening device 6 preferably has at least one piercing element, such as a needle 7, and in the example shown two needles 7.

The capsule chamber 4 preferably has corresponding piercing openings, in this case needle openings 8, for the piercing elements or needles 7. The piercing elements are preferably moved forwards into the piercing openings and close them. This position is assumed by the opening device 6 after the opening of a capsule 3 during the inhalation, in order to seal the piercing openings of the capsule chambers 4 at least to a large extent. However, other types of closure or sealing are also possible, in particular from the interior and/or from the exterior or through autonomously or automatically closing piercing openings or closure devices.

A lateral opening or piercing of the respective capsule 3 preferably takes place. For this purpose, the preferably elongated capsule 3 can be pierced, and thereby opened, longitudinally or laterally and/or transversely with respect to the main flow direction or longitudinal axis of the capsule chamber 4.

Particularly preferably, the capsule 3 is pierced during opening in the region of its two ends and/or laterally.

The piercing or opening of capsules 3 preferably takes place as described in EP 0 147 755 A2, and in this connection reference is hereby made to the content thereof in its entirety.

The opening device 6 preferably has an actuating element 9 which in particular can be actuated manually. The respective capsule 3 can be pierced preferably by actuation or pressing down or pressing in of the actuating element 9.

In the example shown, the piercing elements or needles 7 are preferably firmly connected to the actuating element 9. However, other design solutions are also possible.

The opening device 6 or the actuating element 9 can preferably be actuated against the force of a restoring element, such as at least a spring 10. By means of the restoring element or the spring 10, after the actuation or release of the actuating element 9, the piercing elements or needles 7 preferably resume their retracted starting position, as indicated in FIG. 1. However, other design solutions are also possible.

The inhaler 1 can have a plurality of capsule chambers 4, in each of which a capsule 3 is received and which in each case can in particular be used only once. However, as already mentioned, the inhaler 1 can also have only one capsule chamber 4, in which the capsules 3 are successively received for the discharge or emptying. Thus the capsule chamber 4 is then used multiple times.

The capsule chamber 4 is formed in one or more parts as required. For this purpose, the capsule chamber 4 can also be made up of or produced from different materials and/or by two-component injection moulding.

The capsule chamber 4 preferably has an inlet 11 and an outlet 12 which, in particular axially or on an end face, adjoin an in particular elongated or cylindrical or central movement region or receiving region of the capsule chamber 4 for the capsule 3.

Particularly preferably, the inlet 11 has a reduced diameter relative to the receiving region for the capsule 3, so that preferably an annular shoulder 13 or the like is formed, which forms a stop or a travel limiter for the capsule 3.

The outlet 12 preferably has a securing element 14 associated therewith, which is formed for example in the manner of a grid or a bar and/or prevents a movement of the capsule 3 out of the receiving region or out of the capsule chamber 4.

The geometric conditions preferably correspond at least substantially to the details in EP 0 147 755 A2, which in this connection is hereby introduced as a supplementary disclosure.

During the inhalation or discharge, air or other gas flows through the inlet 11 into the capsule chamber 4, through this or through the receiving region thereof and out of the preferably opposing outlet 12. This stream of air or gas can be produced by breathing in during inhalation and/or by a pressure generator associated with the inhaler 1, such as an air pump, a compressed gas reservoir or the like.

This air stream through the capsule chamber 4 has the effect, in particular due to the Bernoulli effect, that the capsule 3 in the capsule chamber 4 vibrates or oscillates or moves in particular axially to and fro, as indicated by the arrow B in FIG. 1. This movement or vibration B causes or assists the discharge of the formulation 2 from the opened or pierced capsule 3 into the air stream—in particular in the form of very fine particles—and a dispersal of the formulation 2 into the air stream, with which the formulation 2 is finally discharged via the outlet 12 and particularly preferably an adjoining mouthpiece 15 of the inhaler 1, to a user or patient (not shown).

The main discharge direction H of the dispersed formulation 2 by means of the air stream or of the inhaler 1 is indicated in FIG. 1 by a corresponding arrow. Naturally, the discharge is only possible with the cover 18 open and after opening of the respective capsule 3.

The discharge or dispersion of the formulation 2 takes place in particular as described in EP 0 147 755 A2, which in this connection is hereby introduced as a supplementary disclosure. However, in principle the formulation 2 can also be discharged from the capsule 3 in any other suitable manner, for example by rotation of the capsule 3 transversely with respect to the longitudinal axis thereof or the like.

Thus the inhaler 1 preferably has a mouthpiece 15 or some other device for discharging the formulation 2 dispersed in the stream of air or gas.

In the example shown, the mouthpiece 15, in particular a connecting portion 16 thereof, adjoins the capsule chamber 4 or the outlet 12.

Depending upon the requirements and the design, the securing element 14 can be associated with the magazine 5 or the capsule chamber 4 and/or arranged thereon, but if required can also be formed or retained by the inhaler 1 or mouthpiece 15 or connecting portion 16.

The inhaler 1 preferably has a housing 17. This is in particular an external housing.

The mouthpiece 15 is preferably formed or arranged on the housing 17 in particular in a stationary or undetachable manner. However, other design solutions are also possible.

The inhaler 1 or the housing 17 is preferably formed at least substantially in a disc-shaped and/or flat manner.

The mouthpiece 15 is preferably arranged peripherally on the inhaler 1 or housing 17.

The mouthpiece 15 or the main discharge direction H of the inhaler 1 or the movement of the capsule 3 during inhalation preferably extends at least substantially radially to the axis of rotation D of the magazine 5.

The inhaler 1 preferably has a cover 18 associated with the mouthpiece 15 for selective opening and closing of the mouthpiece 15.

With the cover 18 opened, the mouthpiece 15 is freed for inhalation. With the cover 18 closed, as shown in FIG. 1, the mouthpiece 15 is preferably covered. Thus inhalation is not possible.

In the closed position, the cover 18 can optionally, as indicated in FIG. 1, also cover or in some way lock the opening device 6 or the actuating element 9 thereof, in order to rule out or prevent an (undesirable) opening of the capsule 3 in this state by a user.

The cover 18 is preferably retained or mounted pivotably or rotatably (about a pivot axis coaxially with the axis of rotation D or parallel thereto, for example located externally on the housing 17) on the inhaler 1 or housing 17. Alternatively or in addition, the cover 18 is preferably also movable linearly or radially, as is explained in greater detail below.

The cover 18 is preferably connected by positive and/or non-positive engagement, in particular inseparably, to the housing 17 or mounted on or in the housing 17, for example by latching.

After the emptying of a capsule 3 or after the inhalation of the formulation 2 from a capsule 3, the next capsule 3 is brought or moved into the starting position A. This takes place in particular by further movement or rotation of the magazine 5.

If only one capsule chamber 4 is provided for a plurality of or all of the capsules 3, the emptied capsule 3 is first of all moved out of the capsule chamber 4, for example by opening of the capsule chamber 4 on the inlet side. Subsequently, the next capsule 3 can be moved or introduced into the capsule chamber 4 and the capsule chamber 4 can be closed again. This new capsule 3 is then opened or pierced in particular only just before the next inhalation.

On the other hand, there is no need for opening and closing of the capsule chamber 4 if each capsule 3 is received in a separate capsule chamber 4, i.e. it is only necessary for the capsule chambers 4 to be brought or moved together with the capsules 3 in each case individually into the discharge position A.

For use, a user or patient (not shown) opens the inhaler 1 or the cover 18. In this way the mouthpiece 15 is freed. Then the opening device 6 is actuated, i.e. the capsule 3 located in the discharge position A is pierced.

The discharge position A designates in particular a position of the capsule 3 or capsule chamber 4 adjacent to the mouthpiece 15 or the connecting portion 16 thereof.

In the discharge position A, the capsule 3 or the capsule chamber 4 thereof is located in particular in an extension of the connecting portion 16 or mouthpiece 15 and/or with the longitudinal axis thereof aligned with and/or in an extension of the main discharge direction H and/or in the radial direction, in particular relative to the axis of rotation D of the magazine 5.

Inhalation can take place after the opening or piercing of the capsule 3. Subsequently, the inhaler 1 is closed again. The subsequent capsule 3 or capsule chamber 4 is then moved further into the discharge position A, in particular by further movement or further rotation of the magazine 5 to the next capsule 3 or capsule chamber 4.

Various embodiments of the proposed inhaler 1 and magazine 5 are explained in greater detail below, wherein the preceding statements and explanations in particular apply correspondingly or additionally, even if repeated description is omitted.

Figure 2:
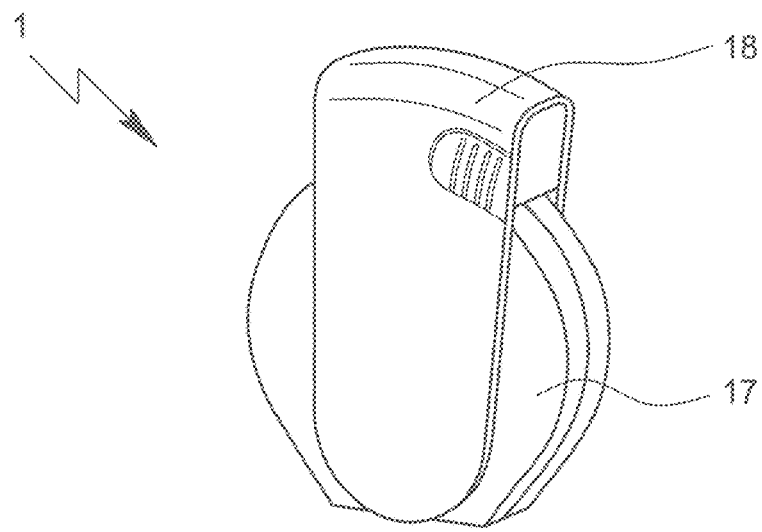
FIG. 2 is a perspective view of a proposed inhaler according to a first embodiment with the cover closed.
Figure 3:
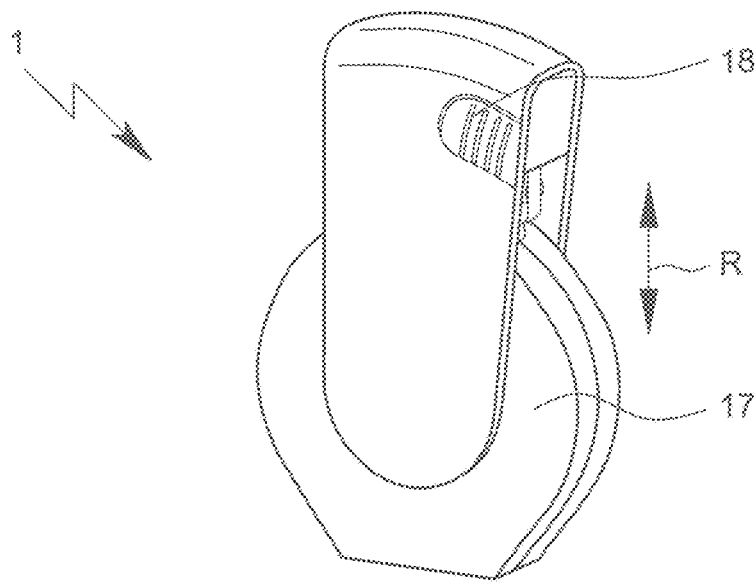
FIG. 3 is a perspective view of the inhaler according to FIG. 2 with the cover pulled out radially.
Figure 4:
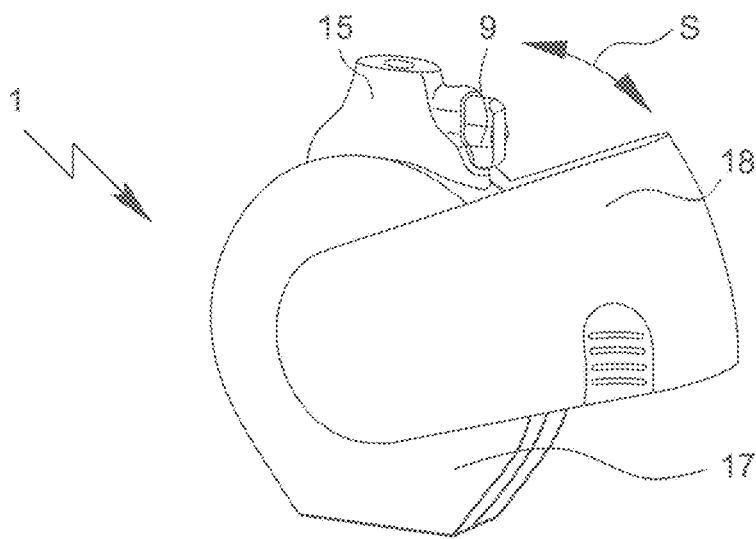
FIG. 4 is a perspective view of the inhaler according to FIG. 2 with the cover opened or pivoted.

FIGS. 2 to 4 show perspective views of a first embodiment of the proposed inhaler 1 in various states.

In FIG. 2, the inhaler 1 or the cover 18 thereof is closed. This is the starting position or closed position.

In FIG. 3, the cover 18 is radially raised or pulled out. This radial movement R forms a first part of the opening movement of the cover 18. In particular, starting from the closed state shown in FIG. 2, first of all only the radial movement of the cover 18 into the position in which it is radially pulled out or moved further away from the mouthpiece 15 is possible, as shown in FIG. 3. This position is also designated below in abbreviated form as the "first opening position" of the cover 18.

The radial movement R extends in particular in the main discharge direction H, so that generally instead of the radial movement R a movement in the main discharge direction H may also be meant.

Starting from the first opening position, the cover 18 is pivoted, in order to free the mouthpiece 15, i.e. to open it, or to open the inhaler 1 completely. This position is also designated below in abbreviated form as the "second opening position" of the cover 18.

FIG. 4 shows this position. The pivoting movement S from the first opening position into the second opening position is indicated by an arrow in FIG. 4.

In the second opening position, the mouthpiece 15 is (completely) freed. Furthermore, in the second opening position the cover 18 frees the opening device 6 or the actuating element 9 thereof, i.e. it no longer covers them, so that manual actuation is now possible.

The pivoting movement S constitutes a second part of the opening movement.

The different parts of the opening movement preferably serve for different purposes or functions.

In particular, the radial movement R or the first part of the opening movement serves in particular for radially moving or conveying the capsule 3 and optionally also an associated capsule chamber 4 out of the magazine 5 into the discharge position A.

In the first embodiment, the discharge position A is located in particular in the mouthpiece 15 or connecting portion 16 and/or preferably radially outside the magazine 5.

The pivoting movement S, in particular from the second or completely opened opening position (FIG. 4) into the intermediate position or first opening position (FIG. 3), i.e. the pivoting of the cover 18, preferably serves for further conveying or further rotation or further cycling of the magazine 5.

Figure 5:
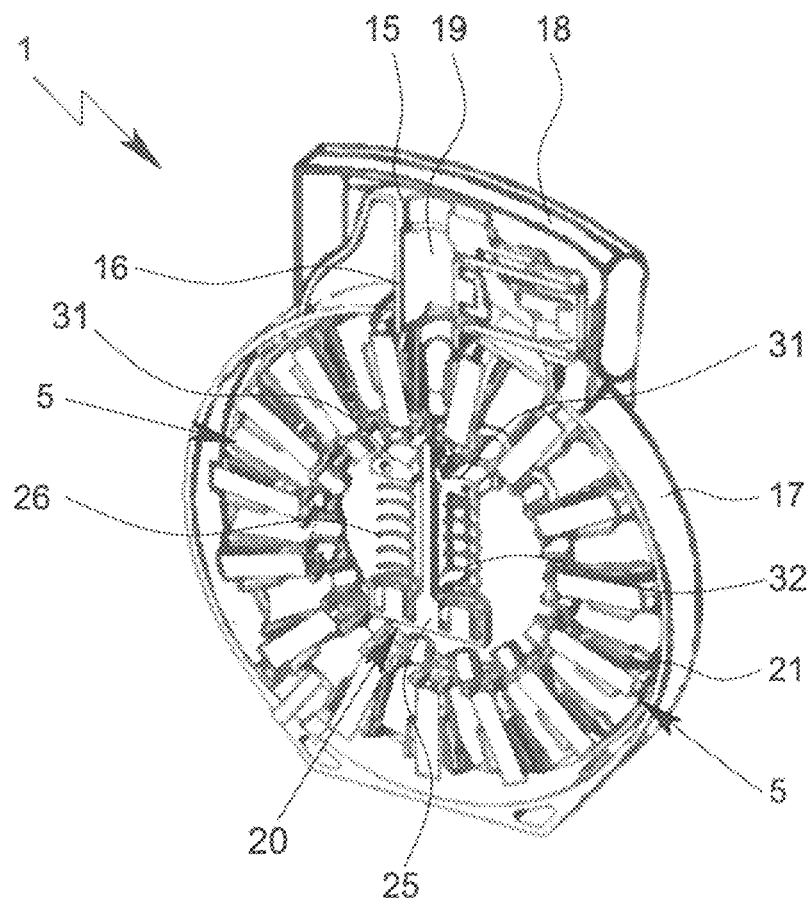
FIG. 5 is a perspective view of the inhaler according to FIG. 2 with the cover closed.

In a schematic section of the inhaler 1 in its main plane E, FIG. 5 shows the preferred structure of the magazine 5 and inhaler 1. The inhaler 1 is located in its starting position.

The inhaler 1 preferably has a receiving chamber 19 for individually receiving a capsule 3 with capsule chamber 4. This receiving chamber 19 is in particular formed by the mouthpiece 15 or the connecting portion 16 thereof and/or defines the discharge position A.

In the representation according to FIG. 5, the receiving chamber 19 is empty, and thus the discharge position A is (still) unoccupied. The cover 18 or the inhaler 1 is located in the closed position or in the starting position.

The capsule chambers 4 can in each case be moved or conveyed individually, together with the respective capsule 3 located therein, out of the magazine 5 radially into the receiving chamber 19 or discharge position A. After the opening of the respective capsule 3 and discharge of the formulation 2 from the opened capsule 3, the capsule chamber 4 is moved back or retracted again into the magazine 5.

In particular for radial movement of the capsule chambers 4 out of the magazine 5 into the discharge position A and/or vice versa, the inhaler 1 preferably has a conveying device 20.

This is preferably arranged at least substantially inside the magazine 5 or in the centre of the magazine 5 and/or inhaler 1.

Figure 6:
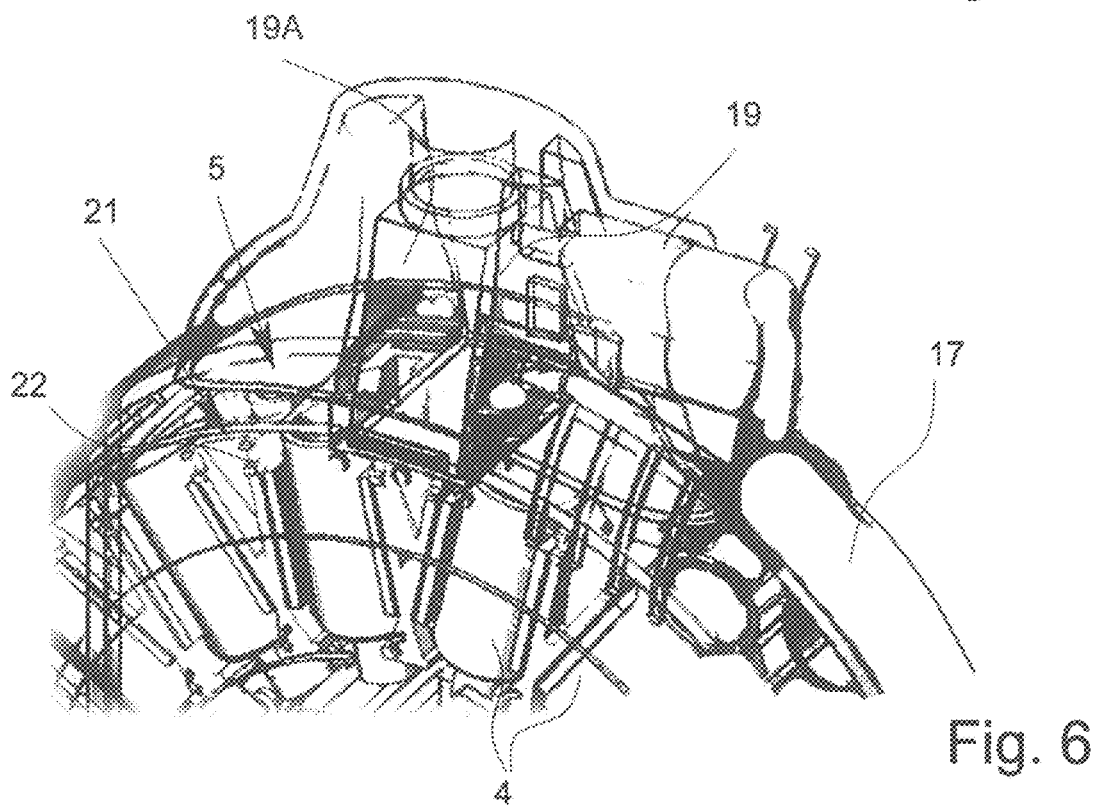
FIG. 6 is an enlarged detail of the representation according to FIG. 5.

FIG. 6 shows, in an enlarged detail of the inhaler according to FIG. 5, a first embodiment of the proposed magazine 5 with adjoining receiving chamber 19.

Figure 7:
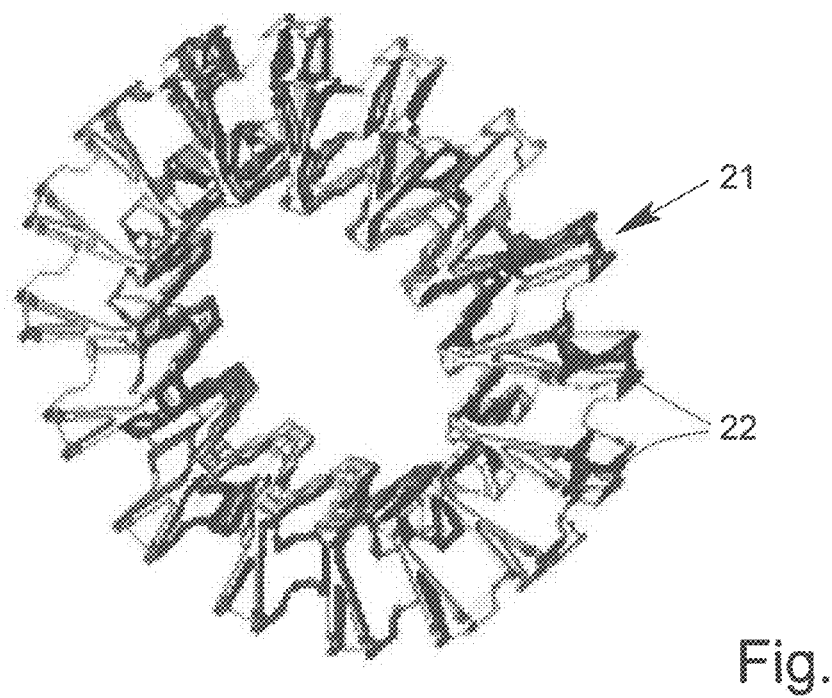
FIG. 7 is a perspective view of a support of the magazine.

The capsule chambers 4 are received in the magazine 5 so as to be radially movable or removable. For this purpose, the magazine 5 preferably has a support 21 shown schematically in FIG. 5 to FIG. 7, in particular wherein the support 21 holds the capsule chambers 4 in the required manner, in particular by clamping and/or locking. For this purpose, the support 21 preferably has corresponding retaining arms or portions 22, as shown in particular in FIG. 6 and FIG. 7.

The capsule chambers 4 are received in the magazine 5 preferably in different planes, in particular in two planes E1 and E2. The two capsule chamber planes E1 and E2 are spaced apart from one another in the axial direction (with respect to the axis of rotation D of the magazine 5) or are arranged offset and/or symmetrically on both sides of the main plane E of the magazine 5. The capsule chamber planes E1 and E2 are indicated schematically in FIG. 21, which will be considered in greater detail later.

The two annular arrangements of capsule chambers 4 in the two planes E1 and E2 are preferably offset or rotated relative to one another in the circumferential direction in such a way that a capsule chamber 4 of one of the planes E1 and E2 always lies between two capsule chambers 4 of the other plane E1 or E2. In particular, the two annular arrangements of capsule chambers 4 or the two planes E1 and E2 are moved somewhat closer together axially. Thus a particularly compact configuration of the magazine 5 is possible or a particularly large number of capsule chambers 4 can be arranged in the magazine 5.

The mouthpiece 15 or the connecting portion 16 or the receiving chamber 19 or the longitudinal axis thereof or the discharge position A is preferably arranged in a plane E3 that is between the two planes E1 or E2 and/or offset relative to the plane E1 and/or the plane E2, in particular in such a way that the capsules 3 or capsule chambers 4 of the plane E1 and/or the plane E2 are guided obliquely out of the magazine 5 into the receiving chamber 19.

The inhaler 1, in particular the mouthpiece 15 or the connecting portion 16 or the receiving chamber 19, preferably has at least one lead-in chamfer 19A or forms such a chamfer, preferably wherein the capsules 3 or the capsule chambers 4 of the plane E1 and/or of the plane E2 can be brought or moved by means of the lead-in chamfer(s) 19A out of the magazine 5 into the receiving chamber 19 or out of the plane E1 or E2 into the discharge position A—preferably offset relative to the plane E1 and/or E2—and/or can be centred during introduction into the receiving chamber 19.

Particularly preferably, the receiving chamber 19 tapers from the inside to the outside or towards the mouthpiece 15, preferably by means of the lead-in chamfer(s) 19A, in particular in such a way that the capsules 3 or capsule chambers 4 are automatically centred during introduction into the receiving chamber 19 or assume the discharge position A, preferably offset relative to the plane E1 and/or E2.

In particular, both the capsules 3 or the capsule chambers 4 of the plane E1 and also the plane E2 can be brought or moved into the same discharge position A, preferably by means of the lead-in chamfer(s) 19A.

Both the capsules 3 or the capsule chambers 4 of the plane E1 and also the plane E2 or all the capsules 3 or capsule chambers 4 are preferably brought by means of the lead-in chamfer(s) in alignment or obliquely into the discharge position A. Here, however, other solutions are also possible, in particular in which only the capsules 3 or capsule chambers 4 of one of the planes E1, E2 must be introduced obliquely into the receiving chamber 19, or the receiving chamber 19 or the longitudinal axis thereof or the discharge position A is located in one of the planes E1, E2.

In the example shown, the magazine 5 preferably has 15 capsule chambers 4 and thus also capsules 3 in each plane E1 or E2 and thus has a total of 30 capsule chambers 4 and capsules 3.

Figure 8:
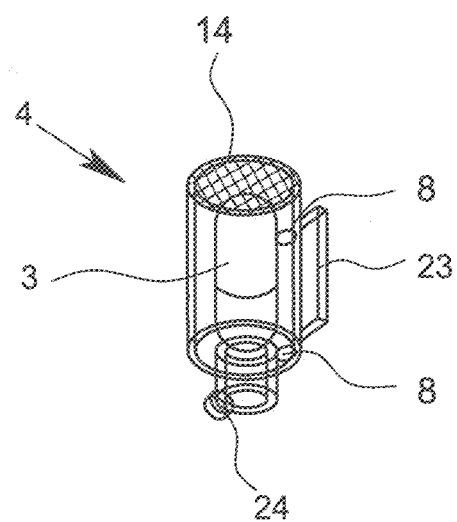
FIG. 8 is a perspective view of a capsule chamber.

FIG. 8 is a perspective view of a capsule chamber 4 in a preferred embodiment. In addition to the lateral needle openings 8, the capsule chamber 4 preferably comprises the securing element 14 for securing the capsule 3 arranged in the capsule chamber 4 against falling out.

The capsule chamber 4 preferably comprises a guide 23 for fixing the rotary position of the capsule chamber 4 in the magazine 5 and/or in the discharge position A or receiving chamber 19. The guide 23 allows the longitudinal displacement or radial movement of the capsule chamber 4, wherein, however, a defined rotary position is assumed at least in the discharge position A, in order to ensure a required rotary position of the needle opening 8 and thus a secure defined engagement of the needles 7 in the needle openings 8 for opening the respective capsule 3. In principle, however, it is also possible that the needles 7 pierce the capsule chamber 4 without defined needle openings 8 being present; in this case the needles 7 puncture the capsule chamber 4 at any location. Then the capsule chamber 4 can also be undefined in its rotary position and for example can be completely rotationally symmetrical and the guide 23 can be omitted.

In the example shown, the guide 23 is formed in particular by at least one corresponding portion on the capsule chamber 4, which preferably extends along the longitudinal axis of the capsule chamber 4 or radial direction of movement of the capsule chamber 4 and/or projects laterally or transversely thereto or is cut out externally on the capsule chamber 4 and/or is formed for example in a rib-like or groove-like manner. A preferably at least substantially complementary possibility for engagement for the guide 23 or of the portion arranged on the capsule chamber 4 is then provided in the magazine 5 or support 21 or in the receiving chamber 19. However, other design solutions are also possible.

Accordingly, the capsule chambers 4 can be moved with a defined rotary position into the discharge position A and/or radially.

The capsule chamber 4 preferably has an engagement portion 24, on which the conveying device 20 can engage. The engagement portion 24 is preferably shaped like a lug and/or a mushroom.

The engagement portion 24 is preferably formed externally on each capsule chamber 4 and/or in the region of the inlet 11.

The engagement portion 24 preferably extends transversely with respect to the longitudinal extent or main axis of the capsule chamber 4 and/or in the circumferential direction or axially in the magazine 5 and/or transversely or perpendicularly to the radial movement R.

The conveying device 20 preferably has a driver 25 and/or a restoring spring 26, as indicated schematically in FIG. 5.

Figure 9:
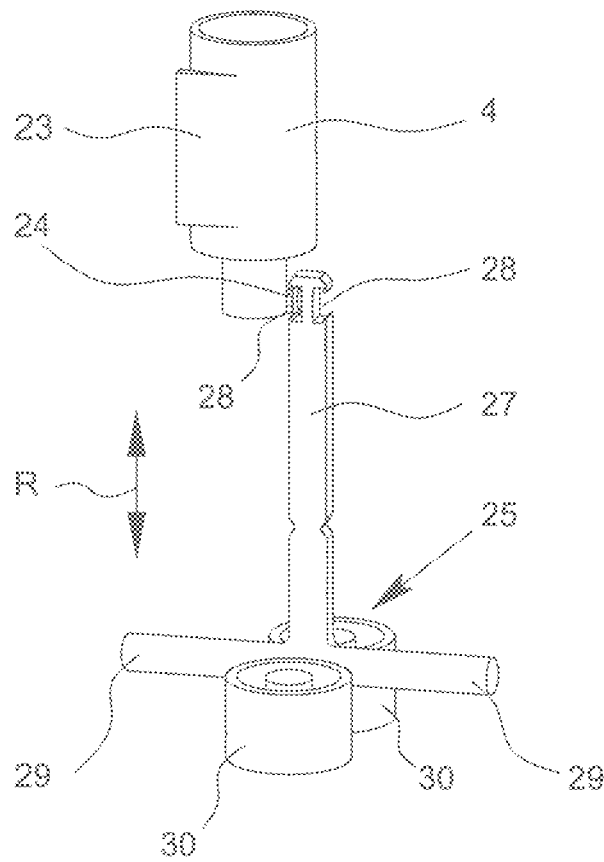
FIG. 9 is a perspective view of a driver of a conveying device with an associated capsule chamber for radial movement of the capsule chamber.

FIG. 9 is a perspective view of the driver 25 and an associated capsule chamber 4, in particular how the driver 25 engages on the capsule chamber 4 or on the engagement portion 24 thereof by means of an engagement element 27, in order to be able to move the capsule chamber 4 radially.

The engagement element 27 is formed in particular like an arm and/or with a cutout 28 for receiving or for engaging the engagement portion 24 of the respective capsule chamber 4.

In the example shown, the cutout 28 is particularly preferably open in the circumferential direction or direction of rotation of the magazine 5 so that, during further rotation of the magazine 5, the respective capsule chamber 4 with its engagement portion 24 can move into the cutout 28, in order to be able to produce the preferably positive engagement in the radial direction, i.e. in the conveying direction of the conveying device 20 or in the direction of the radial movement of the driver 25.

The driver 25 or the engagement element 27 preferably has a cutout 28 on opposite sides in each case, so that alternate capsule chambers 4 from the different planes E1 and E2 can engage alternately in one and the other cutout 28.

The driver 25 extends with its engagement element 27 preferably in the main plane E of the magazine 5 between the two annular arrangements of capsule chambers 4 in the two planes E1 and E2, in particular in order to be able to engage alternately with the capsule chambers 4 in the different planes E1, E2.

The driver 25 preferably has a further engagement element 29 which in particular extends parallel to the axis of rotation D or transversely or perpendicularly relative to the main plane E or radial movement R and/or to the engagement element 27. The further engagement element 29 preferably projects in opposite directions from the driver 25.

The further engagement element 29 is preferably formed like an arm, a bar or a bolt.

The driver 25 preferably has at least one spring seat 30, in the example shown two spring seats 30, to receive or support the restoring spring 26, in this case in particular two restoring springs 26, as indicated in FIG. 5.

The restoring springs 26 with their other ends preferably abut bearing segments 31 of the housing 17. The restoring springs 26 and bearing segments 31 are preferably arranged inside the annular arrangement formed by the magazine 5 or inside the magazine 5 and/or at least substantially in the main plane E.

The restoring springs 26 grip or move the driver 25 into the starting position shown in FIG. 5, i.e. they move the driver 25 into its radially retracted position.

The driver 25 is displaceable longitudinally or radially or in the main discharge direction H in the inhaler 1 or is displaceably or movably guided by the housing 17.

Figure 11:
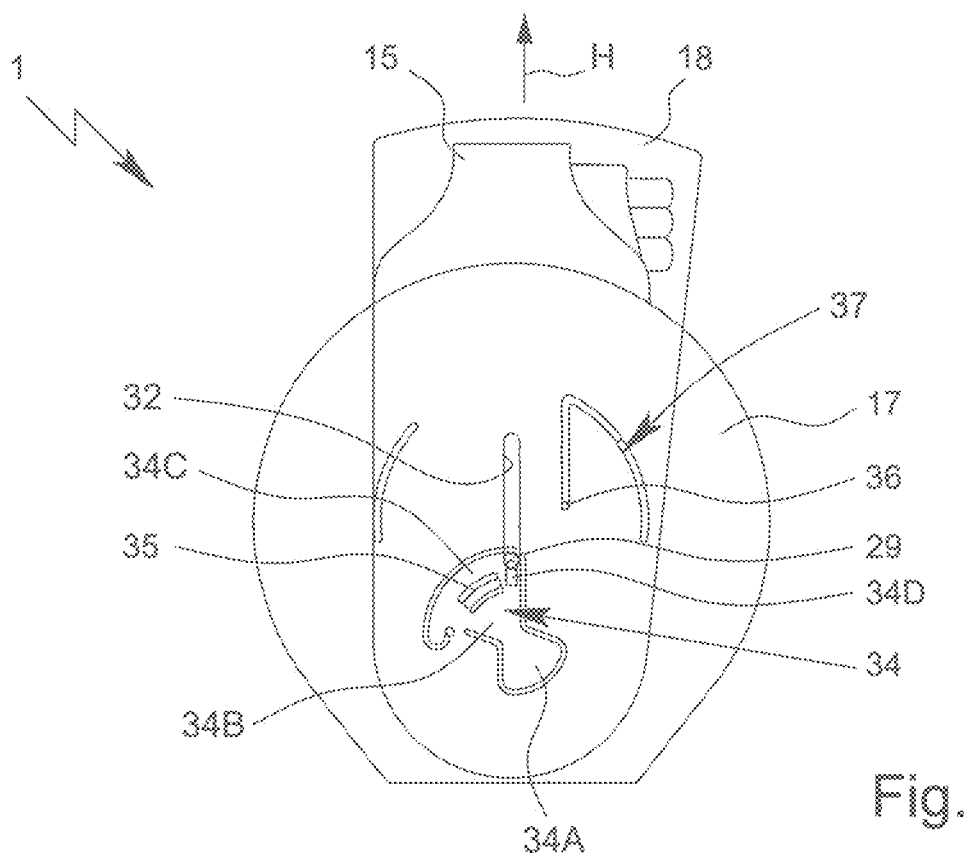
FIG. 11 is a schematic representation of the co-operation of the cover and the driver with the cover pushed in radially.

In the example shown, the driver 25 in particular with its further engagement element 29 passes through a guide slot 32 in the housing 17, as shown in FIG. 11, particularly preferably corresponding guide slots 32 on opposing flat sides of the magazine 5 or housing 17 with the ends of its further engagement element 29 projecting in the opposite direction, so that the driver 25 is correspondingly radially displaceably guided.

The driver 25 or the engagement element 27 thereof can also be displaceably guided, preferably between the two bearing segments 31 and other guide portions of the housing 17 or the like.

Figure 10:
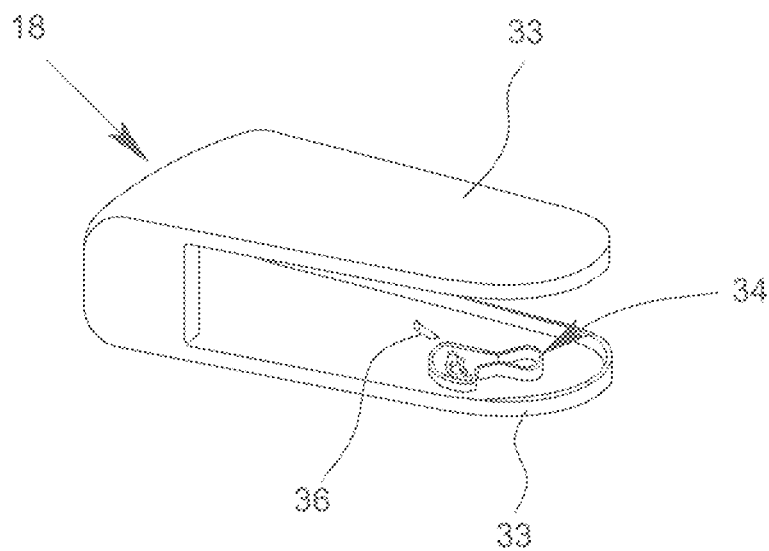
FIG. 10 is a perspective view of the cover without the inhaler.

FIG. 10 is a perspective view of the cover 18. This surrounds the inhaler 1 or the housing 17 preferably at least substantially in a U shape.

The arms 33 of the cover 18 which preferably extend on both flat sides of the housing 17 are preferably flat and/or flank-like and extend to beyond the central axis or axis of rotation D, particularly preferably substantially to close to the peripheral face opposite the mouthpiece 15 or close to the end of the housing 17 in the closed position, as indicated in FIG. 11.

The cover 18 or preferably each arm 33 has in particular (preferably on the inside) a control device or control gate 34 and/or a control element 35 for the driver 25 or a free end of the further engagement element 29 for controlling the radial movement R or the conveying device 20 or the driver 25.

The control element 35 is preferably mounted movably or displaceably in the cover 18, in particular in the control gate 34, preferably in order to guide the further engagement element 29 in the required manner, as is explained in greater detail below.

In the example shown, the two arms 33 are preferably symmetrical, or two-sided guiding and control of the driver 25 takes place.

Figure 18:
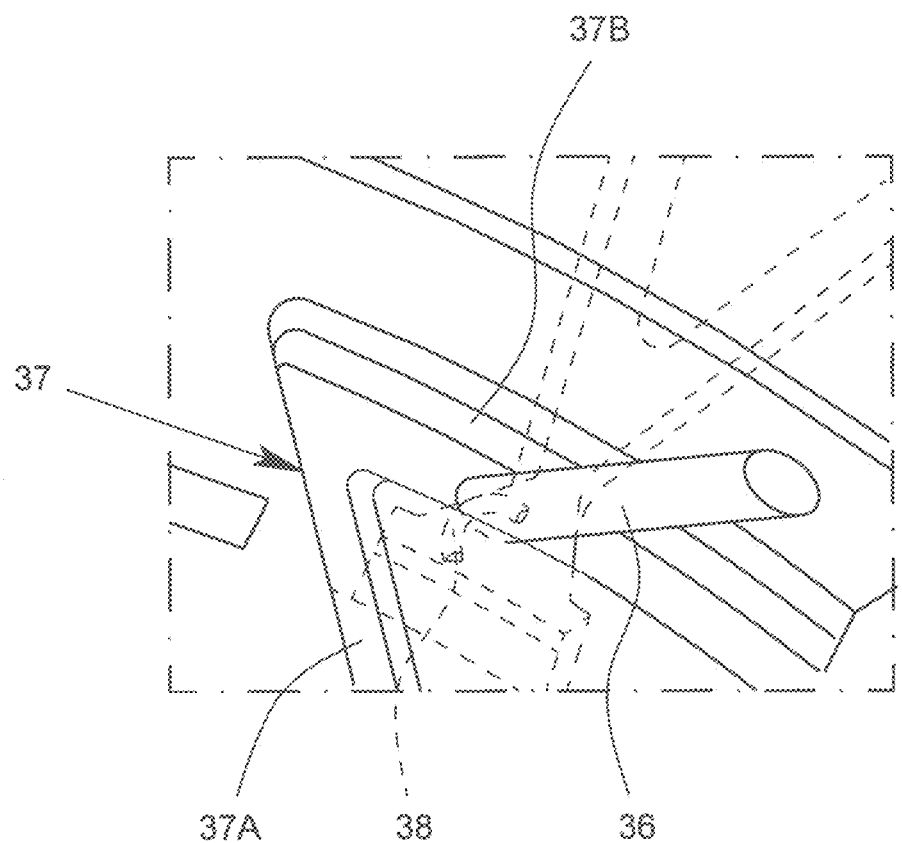
FIG. 18 is a schematic view of the engagement of the cover on the magazine.

The cover 18 or at least one of the arms 33 or each arm 33 also preferably has an in particular arm-like driving element 36 for driving or rotating the magazine 5, as indicated in FIG. 10 or 18. The at least one driving element 36 projects in particular in the manner of an arm and/or inwards and passes through an associated guide gate 37 which is formed in the housing 17 (adjacent to the guide slot 32), as indicated in particular in FIG. 11.

In the following, first of all the preferred control of the radial movement R by movement of the cover 18 is explained in greater detail with the aid of FIGS. 11 to 17. These drawings show the inhaler 1 in a very schematic, partially transparent representation for illustration of the functions in different positions of the cover 18.

FIG. 11 shows the starting position. The cover 18 is located in the closed state, i.e. pushed in radially, and closes the mouthpiece 15.

The control gate 34 preferably has two sector portions 34A and 34B—preferably with the tips pointing towards one another—in particular wherein the sector portions 34A, 34B individually in each case form a gate for the further engagement element 29.

The sector portion 34A or the gate thereof is preferably located radially further inwards than the sector portion 34B or the gate thereof and/or the gate track of the sector portion 34A is longer than the gate track of the sector portion 34B.

The control gate 34 or the sector portion 34B preferably forms an annular groove portion 34C which extends in the circumferential direction and is preferably partially delimited by the control element 35 which is movable in the circumferential direction relative to the control gate 34 and can be opened inwards.

In the starting position, the further engagement element 29 is preferably located in a corner of the sector portion 34B or at the start of the annular groove portion 34C or a circular path formed thereby, preferably wherein a movement of the further engagement element 29 relative to the cover 18 in the direction of the tip of the sector portion 34B or in the radial direction is not possible because of a preferably ramp-like retaining lug 34D which is formed in particular in the cover 18.

Figure 12:
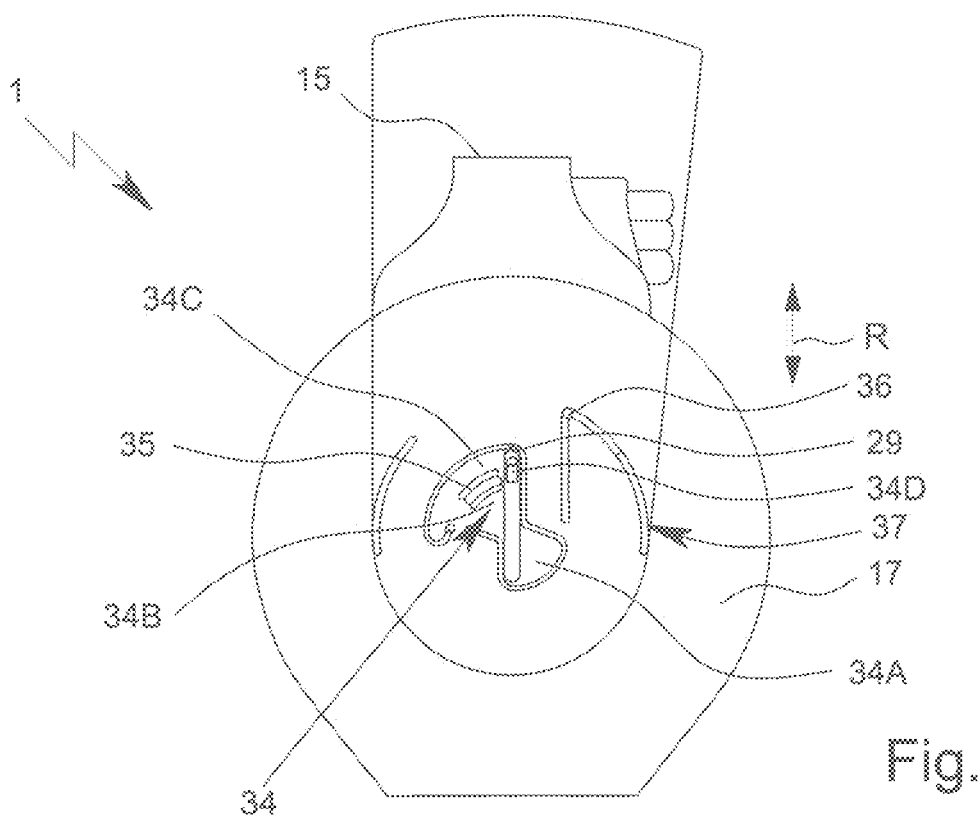
FIG. 12 is a schematic representation of the co-operation of the cover and the driver with the cover pulled out radially.

When the cover 18 is pulled out radially, i.e. during the first part of the opening movement or during the radial movement R, the further engagement element 29 and the driver 25 are entrained by the retaining lug 34D or control gate 34 and are moved radially in the direction of the mouthpiece 15 or in the main discharge direction H. In this case, the further engagement element 29 is displaced along the guide slot 32. FIG. 12 shows the first opening position which then results.

As a result, the radial movement R of the cover 18 preferably causes a radial movement R of the conveying device 20 or of the driver 25 and thus the required radial movement R or conveying of the associated capsule chamber 4 (i.e. the capsule chamber 4 currently engaged with the conveying device 20 or the driver 25) into the discharge position A or receiving chamber 19.

The conveying device 20 or the driver 25 or the engagement element 27 preferably retains or secures the respective capsule chamber 4 in the discharge position A, in particular until the inhalation has taken place or until the inhaler 1 or the cover 18 thereof is closed again. The restoring movement preferably takes place by means of the restoring spring(s) 26, which will be considered in greater detail below.

After the first opening position is reached, the cover 18 is pivoted up, i.e. it carries out the pivoting movement S.

Figure 13:
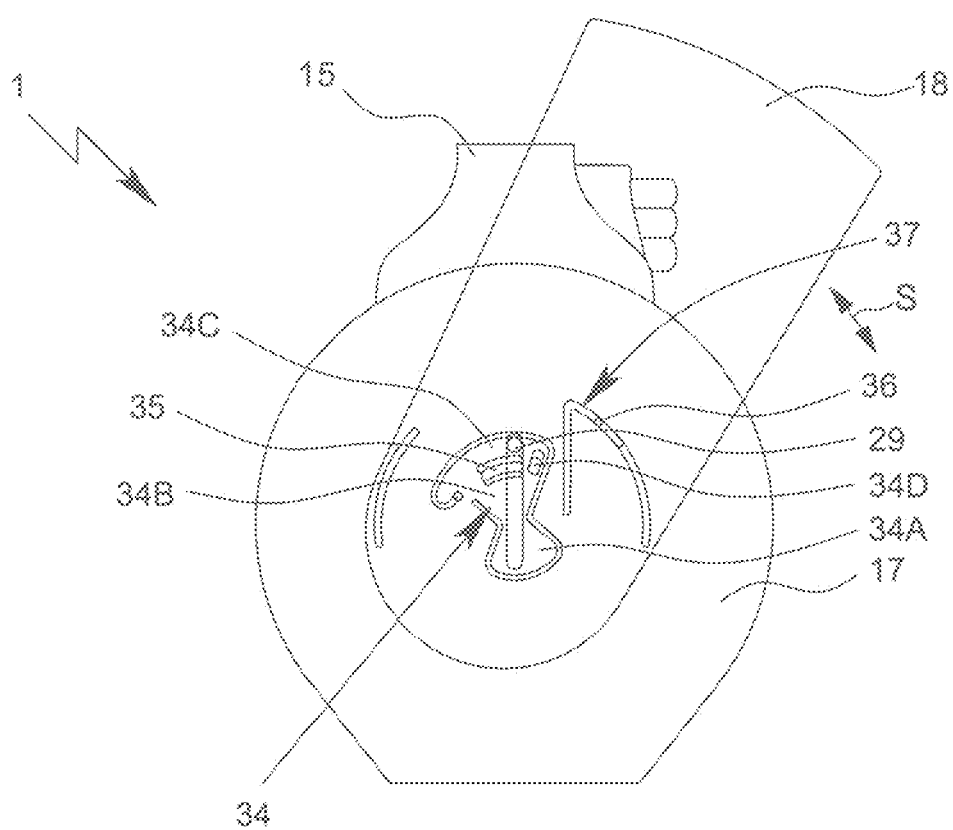
FIG. 13 is a schematic representation of the co-operation of the cover and the driver with the cover slightly pivoted.

FIG. 13 shows an intermediate position between the first opening position and the completely opened second opening position. The further engagement element 29 now travels along the annular groove portion 34C or the circular path, preferably wherein the radially inner limiter and also, in the further course of the opening movement or the circular path, the radially inner control element 35 ensure that the conveying device 20 or the driver 25 are retained in the radially advanced position and thus also the associated capsule chamber 4 is retained in the discharge position A, or a restoring movement of the further engagement element 29 out of the annular groove portion 34C into the sector portion 34A is prevented.

Figure 14:
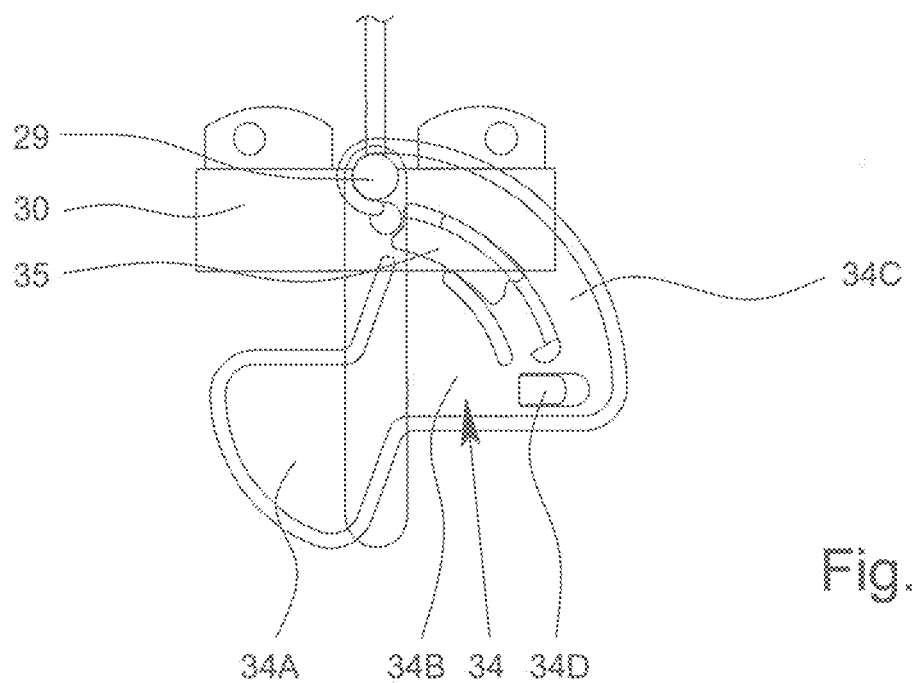
FIG. 14 is a schematic representation of the co-operation of the cover and the driver with the cover completely opened.

FIG. 14 shows the state with the completely opened cover 18, i.e. when the second opening position is reached. The further engagement element 29 is now located at the end point of the circular path or of the annular groove portion 34C and furthermore is retained there against a radial return movement inwards from the inner side wall of the annular groove portion 34C.

It should be noted that the inner wall of the annular groove portion 34C is partially interrupted or has an interruption 34E, preferably wherein the interruption 34E is broader than the further engagement element 29 or the diameter thereof. The centre angle of the interruption 34E is preferably more than 5° or 10° and/or less than 20° or 15°.

During the opening operation, this interruption 34E is bridged by the control element 35 so that, during opening of the cover 18 by pivoting, the driver 25 is continuously retained in its radially advanced position. During the closing operation or pivoting back of the cover 18, the control element 35 is pressed by the driver 25 or further engagement element 29 in the direction of the retaining lug 34D, in particular in such a way that the interruption 34E is freed or the further engagement element 29 is preferably moved downwards or radially inwards or into the sector portion 34A by spring force or automatically, as is explained in greater detail below.

In the opened position of the cover 18, the opening device 6 or the actuating element 9 thereof is freely accessible. Now the opening or piercing of the capsule 3 located in the discharge position can take place by actuation of the actuating element 9.

The inhalation takes place after the opening or piercing of the capsule 3.

Subsequently, the inhaler 1 or the cover 18 thereof is closed again.

Figure 15:
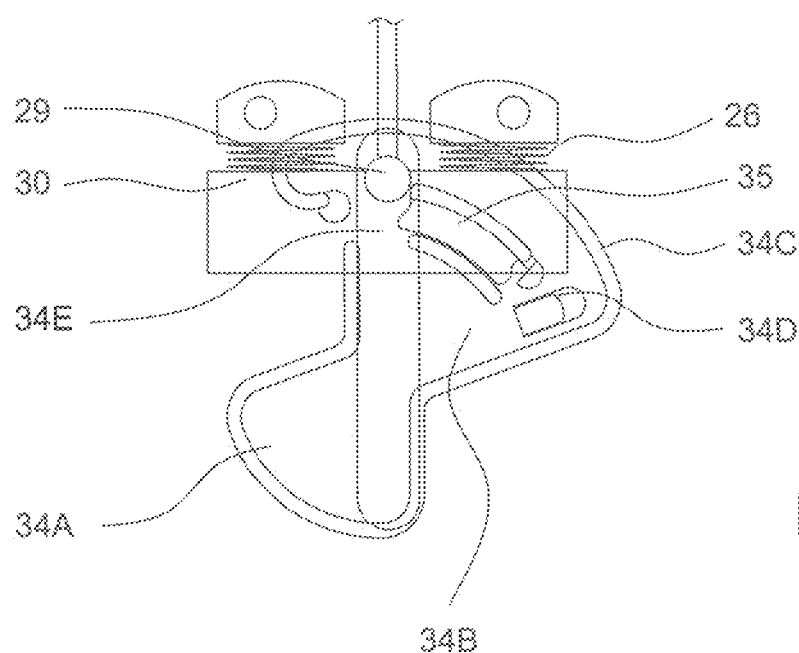
FIG. 15 is a schematic representation of the co-operation of the cover and the driver upon initial closing of the cover.

FIG. 15 shows an intermediate state shortly after the initial closure of the cover 18. The further engagement element 29 has just reached the interruption 34E. In this return movement or closing movement, the control element 35 is initially not entrained by the cover 18, but can move relative thereto or relative to the arm 33 thereof in a guide groove or the like extending in a circumferential direction, so that the interruption 34E is freed is and/or the further engagement element 29 can be moved radially inwards.

The driver 25 is now moved back again into its retracted position, i.e. moved radially inwards, by the force of the restoring spring(s) 26. Thus the further engagement element 29 is moved radially inwards again along the guide slot 32. In this case, the further engagement element 29 moves into the sector portion 34B and subsequently into the following sector portion 34A.

Figure 16:
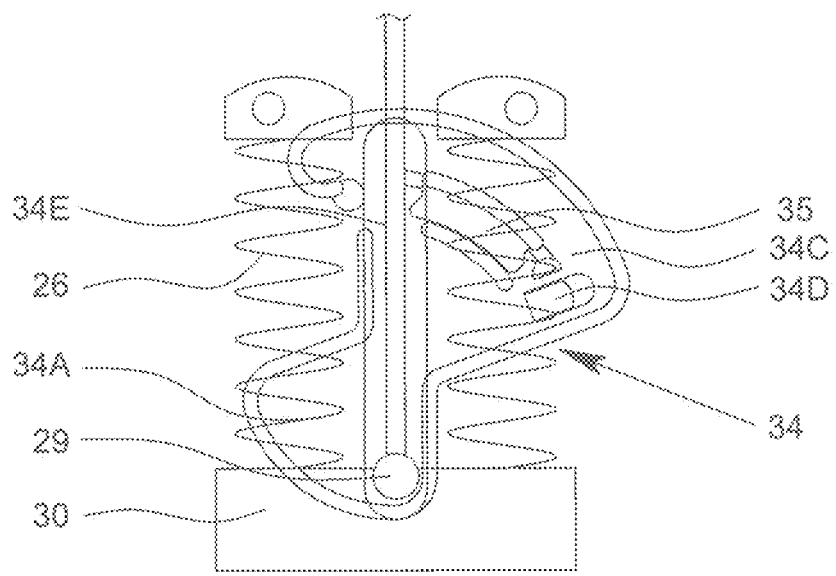
FIG. 16 is a schematic representation of the co-operation of the cover and the driver with the driver moved back again radially.

FIG. 16 shows the position which is then assumed.

The return of the driver 25 also causes the radial return movement or the movement back of the capsule chamber 4 into the magazine 5. Thus this preferably takes place by spring force and/or during closing or pivoting back, in particular during initial closing of the cover 18.

Figure 17:
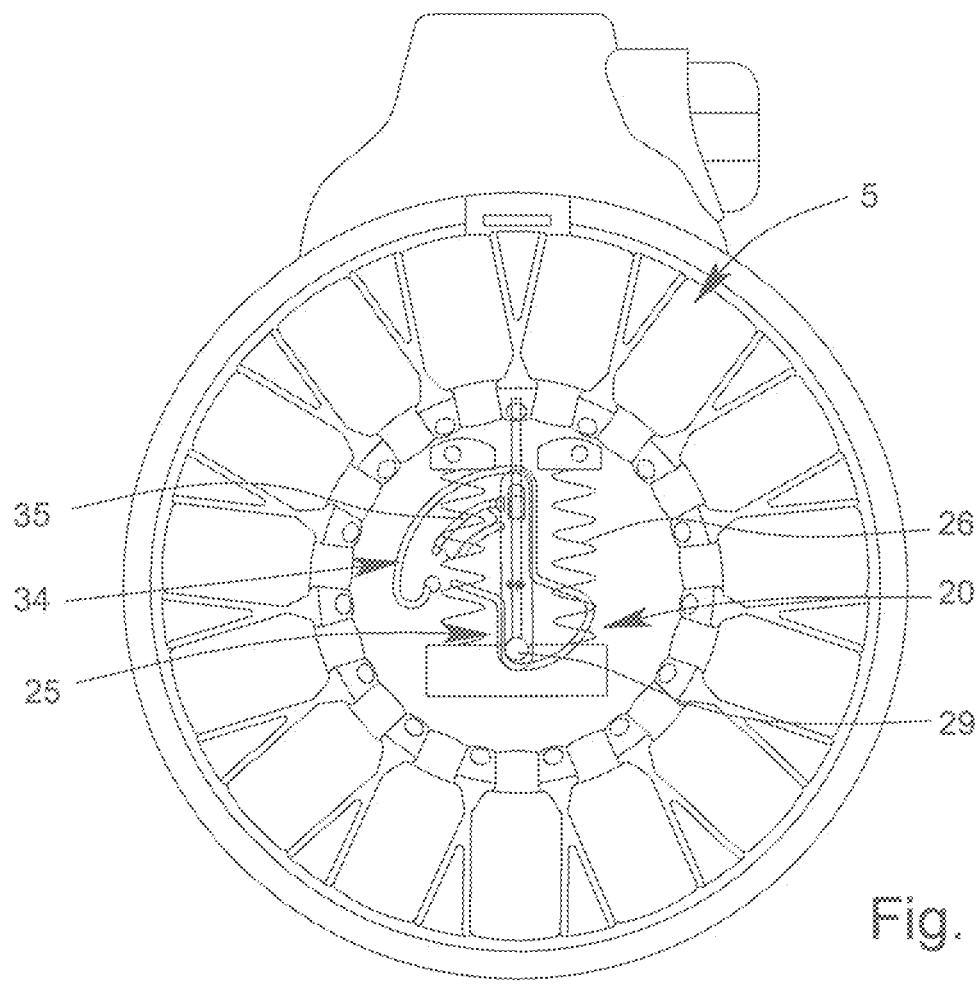
FIG. 17 is a schematic representation of the co-operation of the cover and the driver with the cover pivoted back into the closed position but not yet pushed in radially.

FIG. 17 shows the state when the cover 18 has been completely pivoted back again into the first opening position. During pivoting, the further engagement element 29 moves along the outer circumference of the sector portion 34A or of the gate thereof into the position shown in FIG. 17. This position now lies radially relative to the starting position of the further engagement element 29 in the other sector portion 34B as shown in FIG. 11.

When the cover 18 is pushed in radially, i.e. the cover 18 is completely closed (in order to reach the position shown in FIG. 11), the further engagement element 29 remains in its retracted radial position in the guide slot 32, but moves relative to the control gate 34 or into the sector portions 34A and 34B, wherein towards the end it travels over the retaining lug 34D, which in particular moves axially outwards (together with the arm 33 or the cover 18, as applicable), until the starting position shown in FIG. 11 is reached again.

The retaining lug 34D or the undercut or stop formed thereby then ensues that if the cover 18 later moves out radially the further engagement element 29 is radially entrained or moved therewith, i.e. pulled radially outwards, in order accordingly to move the driver 25 and the associated (next) capsule 3 or capsule chamber 4 radially with respect to the discharge position A or into the discharge position A.

Preferably, when the cover 18 is pushed out radially, a new capsule 3 or capsule chamber 4 is consequently brought into the discharge position A or provided for the discharge, in particular by a positively engaged connection between the cover 18 or the retaining lug 34D thereof and the driver 25 or the further engagement element 29 thereof. In this way a new actuation cycle begins.

The driver 25 or the further engagement element 29 is preferably guided and moved, in each case as explained above, on both sides of the cover 18 or the arms 33 thereof or corresponding control gates 34.

The further movement or further rotation of the magazine 5 or the coupling of the pivoting movement of the cover 18 to the magazine 5 is explained in greater detail below.

In order to change from one capsule 3 or capsule chamber 4 to the next capsule 3 or capsule chamber 4 or to provide the next capsule 3 or capsule chamber 4 for the delivery, the magazine 5 can preferably be rotated or driven, in particular by pivoting of the cover 18.

The further movement or further rotation of the magazine 5 to the next capsule chamber 4 preferably takes place during closing of the cover 18, in particular by the closing movement or the pivoting in the closing direction, particularly preferably towards the end of the pivoting movement S during closing, just before the first opening position is reached and/or immediately after freeing of the interruption 34E by displacement of the control element 35 and/or immediately after the restoring movement of the driver 25 or after the movement of the used capsule 3 or capsule chamber 4 back into the magazine 5.

In particular, the pivoting movement S of the cover 18 in the closing direction first of all, or during the initial pivoting movement S, results in freeing of the interruption 34E or restoring of the driver 25 or a return of the used capsule 3 or capsule chamber 4 back into the magazine 5 and only then or upon further pivoting or towards the end of the pivoting movement S a further movement or further rotation of the magazine 5 to the next capsule 3 or capsule chamber 4 take place. In this way by means of a—preferably uninterrupted and/or consistent—pivoting movement S, both a return of the used capsule 3 or capsule chamber 4 back into the magazine 5 and also a further movement of the magazine 5 can be achieved, in particular without the two movement sequences being superimposed.

During opening or closing, the cover 18 is preferably pivoted overall by more than 60, in particular substantially 80 to 90° or more. The further movement or further rotation of the magazine 5 takes place in each case only by a substantially smaller angle, in the example shown with a total of 30 capsule chambers 4 in each case only by 12°. Accordingly, it is necessary and desirable that the pivoting movement S of the cover 18 is coupled only partially or temporarily to the magazine 5. Furthermore, as a result the initial pivoting movement S of the cover 18 can take place during closing for release or causing the (radial) return movement into the magazine 5 of the capsule chamber 4 (with emptied capsule 3) which is located in the starting position A.

The guide gate 37 is preferably formed by a slot-like opening in the housing 17. It has in particular a linear radial portion 37A and a curved portion 37B adjoining it in the circumferential direction, as indicated in the detail according to FIG. 18.

Starting from the two flat sides of the inhaler 1, in each case with a driving element 36 (formed internally on the cover 18), the cover 18 or the arms 33 thereof in each case preferably engages in a respective associated guide gate 37 and serves for the required driving of the magazine 5, wherein the driving elements 36 can also engage, where appropriate, alternately on both sides on the magazine 5, in order to be able to drive the magazine 5 in the required manner, in this case in particular in 12° steps.

The driving element 36 is preferably arranged internally on the cover 18 or on a side facing the housing 17.

Preferably, the driving element 36 is formed integrally with the cover 18 and/or is formed on the cover 18. The driving element 36 is preferably designed to be at least partially flexible and/or oriented obliquely relative to an arm 33, preferably in such a way that the driving element 36 can be connected by positive and/or non-positive engagement to the drive portion 38 exclusively in one direction of movement and/or a ratchet-like connection is formed between the driving element 36 and the drive portion 38.

The guiding of the driving element 36 of the cover 18 in the guide gate 37 and/or the engagement of the further engagement element 29 in the control gate 34 can serve in each case for a desired or necessary support for the cover 18 on the inhaler 1 or housing 17. However, other structural solutions for the support can also be used alternatively or additionally.

FIGS. 11 to 13 show the movements of a driving element 36 in the associated guide gate 37 during the opening of the cover 18 or in the different states.

FIG. 18 shows the engagement of the driving element 36 on the magazine 5, in particular on a drive portion 38 of the magazine 5, in order to rotate this further. The drive portion 38 is in particular a stop which springs forwards or backwards axially, so that the driving element 36 arriving in the circumferential direction can engage positively in order to be able to rotate the magazine 5 during the closing movement—i.e. during the movement along a part of the curved portion 37B.

The drive portion 38 is preferably partially circular. However, other solutions are also possible. By the subsequent radial movement R during the radially inward movement along the radial portion 37A—i.e. during the radial closure of the cover 18—the driving element 36 is released or disengaged from the drive portion 38 or the stop formed thereby.

During opening of the cover 18, the driving element 36 is moved in the opposite direction. It is moved away by means of the next drive portion 38—preferably by means of an axially inclined crooked plane or sliding surface which can also be formed in particular by a capsule chamber 4—preferably in such a way that the driving element 36 or the cover 18 and the arms 33 thereof and/or the respective drive portion 38 diverge or spring out axially in order to allow the travel.

If the opening movement of the cover 18 is so great that the driving element 36 travels over a further drive portion 38 on the magazine 5, the driving element 36 is preferably raised or disengaged axially from the guide gate 37 in such a way that a premature engagement with the further drive portion 38 does not take place during the closing movement.

During closing of the cover 18, i.e. during pivoting, the required engagement on the one traversed drive portion 38 by the driving element 36 then takes place, in order to cycle the magazine 5 by a further position, i.e. to rotate it further to the next capsule 3 and capsule chamber 4 (now in the respective other plane E1 or E2).

Figure 19:
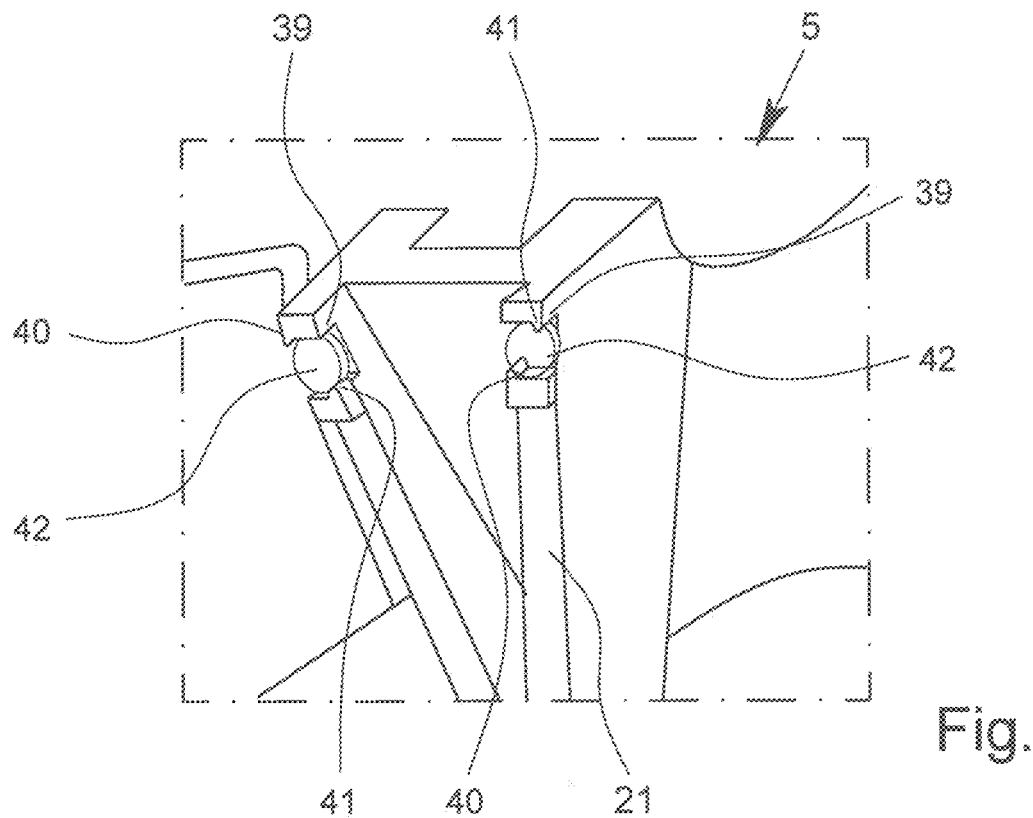
FIG. 19 is a schematic representation of a return rotation lock of the magazine by engagement of projections of the housing on the magazine or support.

The inhaler 1 preferably has a device for securing the magazine 5 against undesirable turning back and/or for defined positioning in each case of the magazine 5 in the different rotary positions (for individual orientation of the capsule chambers 4 relative to the receiving chamber 19 or to the mouthpiece 15 or to the discharge position A). For this purpose, in the example shown further cutouts 39 having ribs 40 which run forwards and ribs 41 which run backwards are preferably formed axially and in the circumferential direction on the magazine 5 or on the support 21 thereof, as indicated in FIG. 19, and co-operate with preferably knob-like and/or axial projections 42 on the housing 17 in such a way that in the required rotated position in each case one or more projections 42 engage in the further cutouts 39, and the ribs 40, 41 prevent a further rotation and/or turning back by corresponding abutment on the associated projection 42, and/or further rotation in only one direction is made possible by asymmetric shaping and/or deformability of the ribs 40, 41. However, other structural solutions are also possible.

Figure 20:
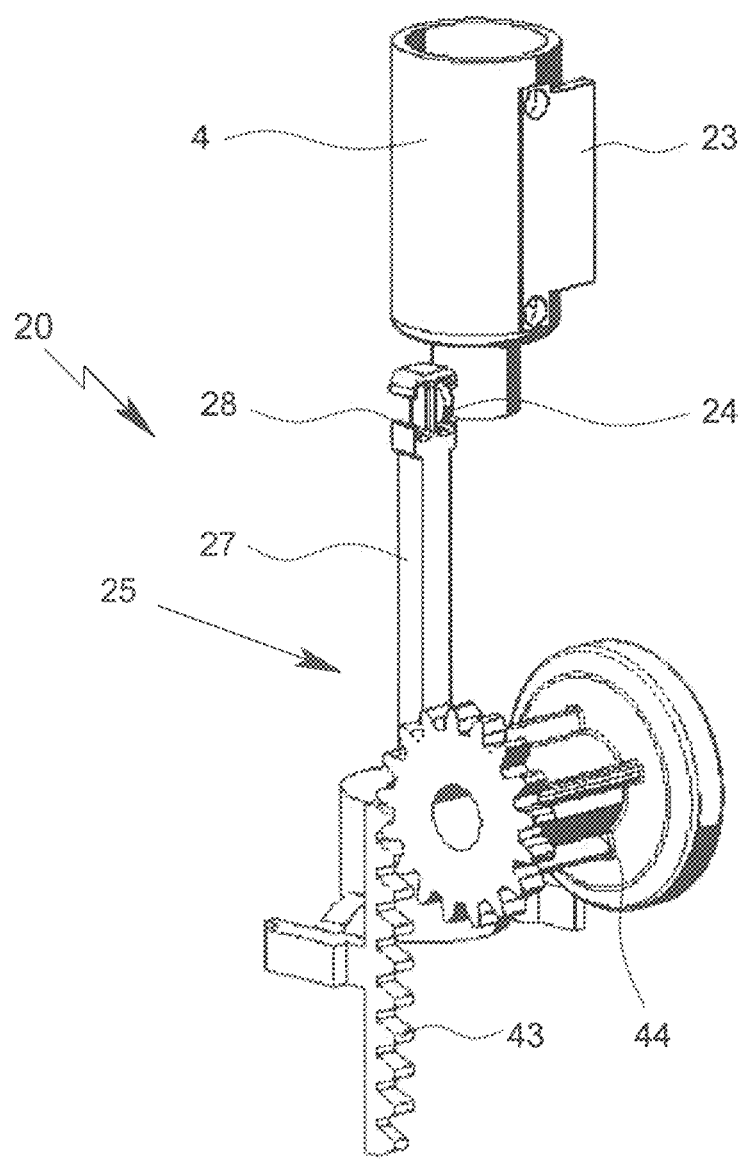
FIG. 20 is a perspective view of an alternative driver.

An alternative embodiment of the conveying device 20 or the driver 25 is shown schematically in a perspective drawing in FIG. 20. Here the driver 25 is configured like a toothed rack or is provided with a toothed rack 43, which is movable in the required manner linearly or in the radial direction by means of a gear 44 which can be driven in a suitable manner by the cover 18.

Preferably in such an embodiment, the gear 44 is connected or coupled to the cover 18 or the arm 33 thereof by positive and/or non-positive engagement, in particular in such a way that a pivoting movement of the cover 18 leads to a rotation of the gear 44 or radial movement of the driver 25.

In particular in such an embodiment, a pivoting movement of the cover 18 is exclusively provided or the pivoting movement of the cover 18 is converted into a radial and/or linear movement of the driver 25, preferably in such a way that a radial movement of the cover 18 and/or the gear 44 is omitted.

Preferably during a pivoting movement by the cover 18, the gear 44 is only driven portion by portion by the cover 18, or the gear 44 is connected to the cover 18 by positive and/or non-positive engagement only portion by portion or in a defined angle range, for example by means of a clutch with freewheel and/or a self-releasing clutch. Thus the connection between the cover 18 and the gear 44 can be released for example by a pivoting movement S for closing the inhaler 1 and the driver 25 can be moved radially inwards by means of spring force. In this way—by analogy with the first embodiment—by means of a—preferably uninterrupted and/or consistent—pivoting movement S both a return of the used capsule 3 or capsule chamber 4 back into the magazine 5 and also a further movement of the magazine 5 can be achieved, in particular without the two movement sequences being superimposed.

Further embodiments of the proposed inhaler 1 and the proposed magazine 5 are explained below, wherein the previous statements and explanations in particular with regard to the first embodiment also apply correspondingly or additionally to the further embodiments, even if corresponding repetitions are omitted. The following statements and explanations are therefore limited in particular to significant new aspects or to differences.

Figure 21:
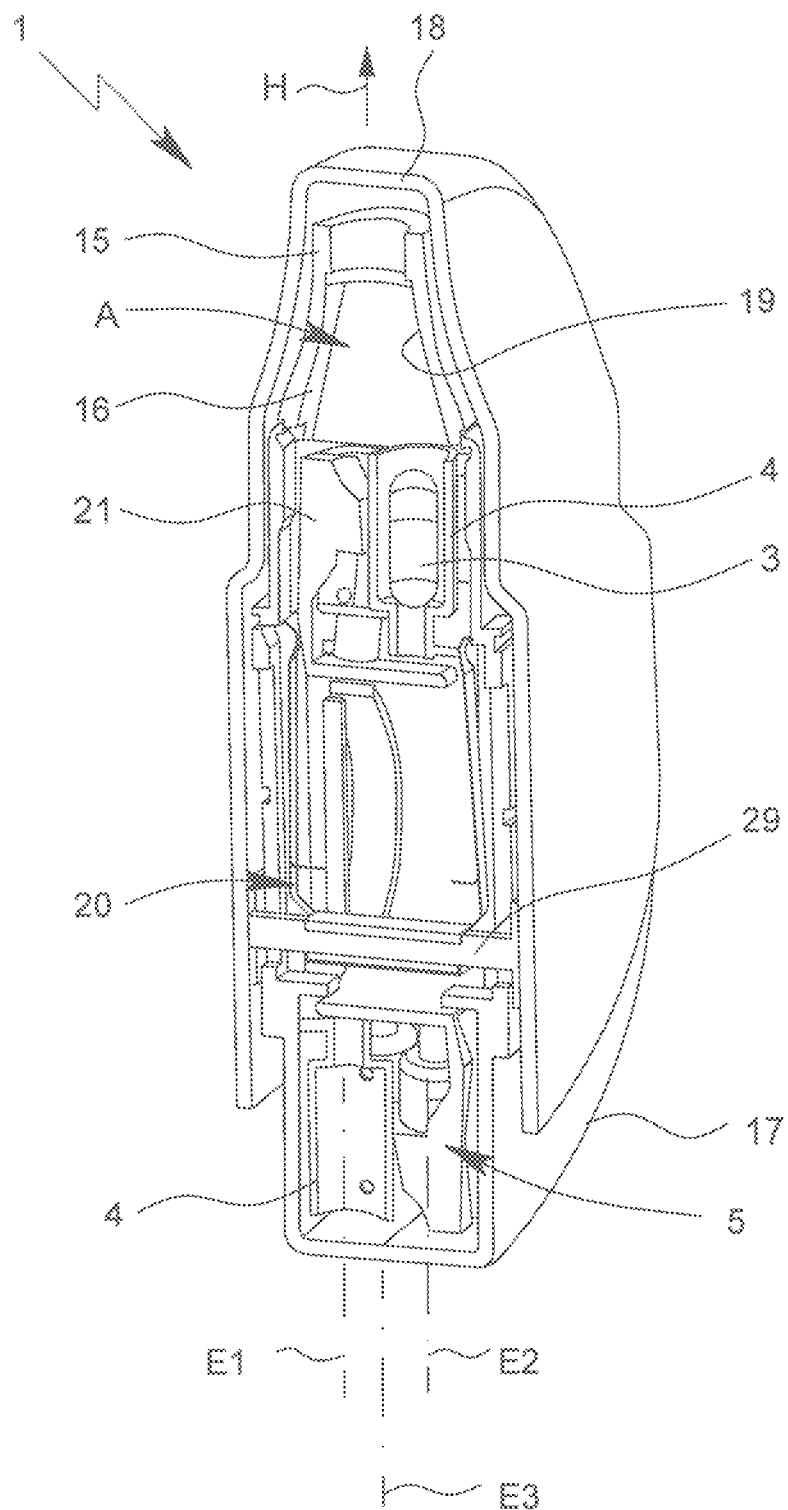
FIG. 21 is a schematic section through a proposed inhaler according to a second embodiment.

FIG. 21 shows a second embodiment of the proposed inhaler 1 in a section perpendicular to the main plane E, i.e. perpendicular to the section according to FIG. 5.

In the second embodiment, the driver 25 is configured differently, in particular as a stamped or bent part made of metal.

Figure 22:
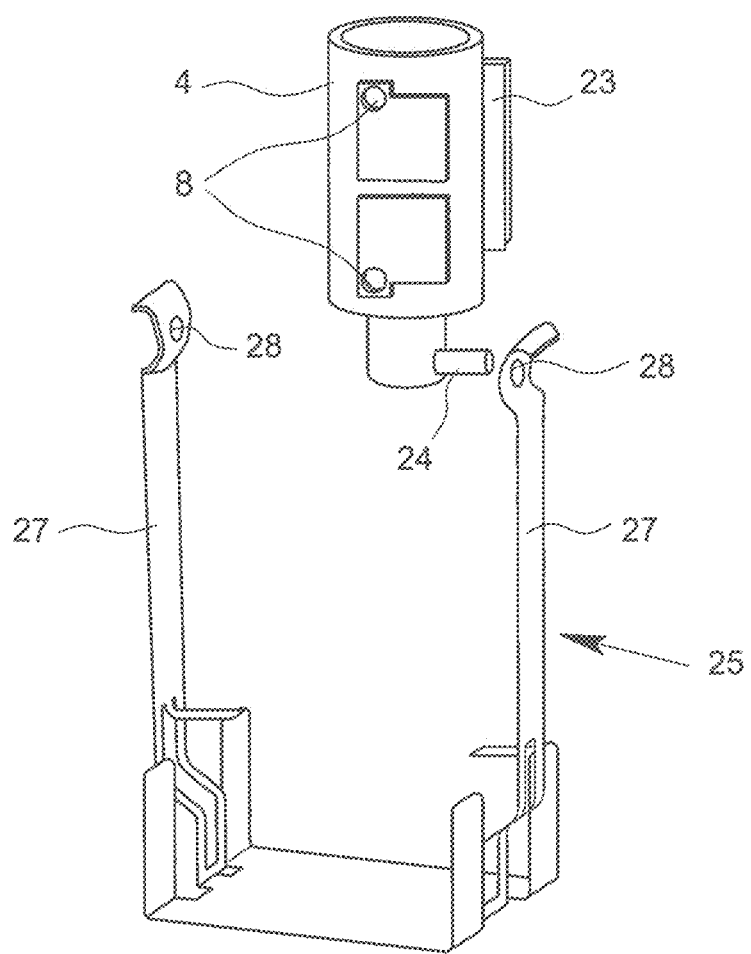
FIG. 22 is a perspective view of the driver of the inhaler according to FIG. 21 with associated capsule.

FIG. 22 shows the driver 25 in the uninstalled state with an associated, but not yet engaged, capsule chamber 4.

The driver 25 is in turn displaceable in the radial direction in the inhaler 1 or housing 17 by means of an further engagement element 29, which is coupled to the driver 25 and only shown in FIG. 21, in order to the move capsule chambers 4 individually out of the magazine 5 (at least substantially) radially into the receiving chamber 19 or discharge position A and preferably back.

The driver 25 here has two engagement elements 27 which are spaced apart axially and can be bent inwards in the axial direction or relative to one another, with in each case a cutout 28 in the region of the free end.

FIGS. 21 and 22 show the starting state. Here, the conveying device 20 or the driver 25 is still located in the radially retracted position. The respective engagement element 27 and the respective capsule chamber 4 are not yet in engagement with one another.

Figure 23:
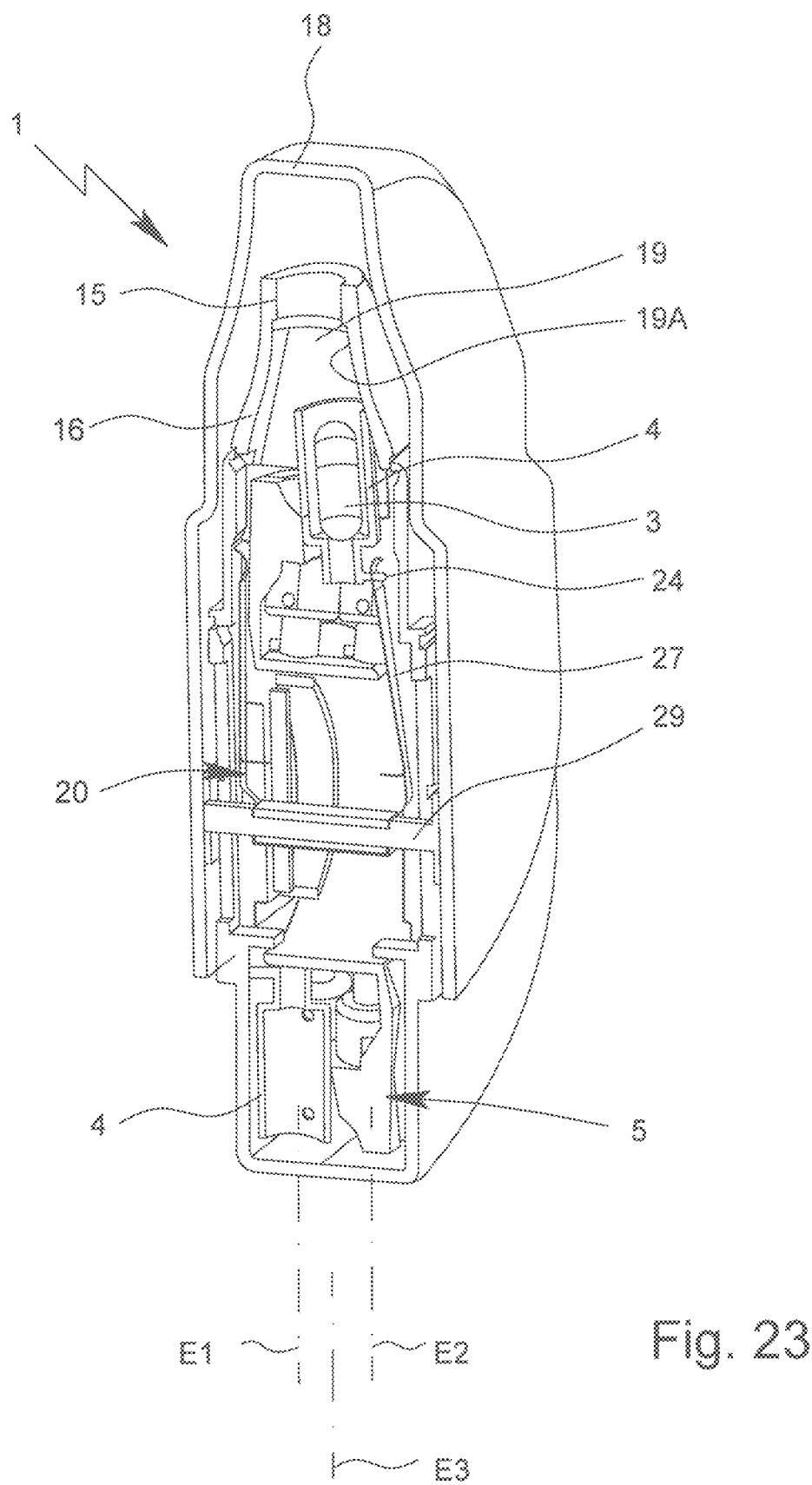
FIG. 23 is a schematic section through the inhaler according to FIG. 21 with the cover partially pulled out radially.

FIG. 23 shows, in a step corresponding to FIG. 21, an intermediate state during partial radial movement R of the cover 18 and of the driver 25. The corresponding engagement element 27, in this case the right-hand engagement element 27, has been deflected axially inwards by the housing 17 or another component and thereby brought into engagement with the associated capsule 4, so that the engagement portion 24 of this capsule chamber 4 engages in the cutout 28 of this engagement element 27.

Furthermore, it can be seen in FIG. 23 that the capsule chamber 4 has already been partially moved out of the magazine 5 and its plane E2 and is slightly tilted relative to the main plane E. In this case in particular, the mouthpiece 15 or the connecting portion 16 or the inner wall of the receiving chamber 19 serves as a guide, in order to guide the respective capsule chamber 4 out of the respective plane E1 or E2 into the main plane E and finally to orient it as required, in particular in the plane E or in an extension of the mouthpiece 15 or the main discharge direction H.

Figure 24:
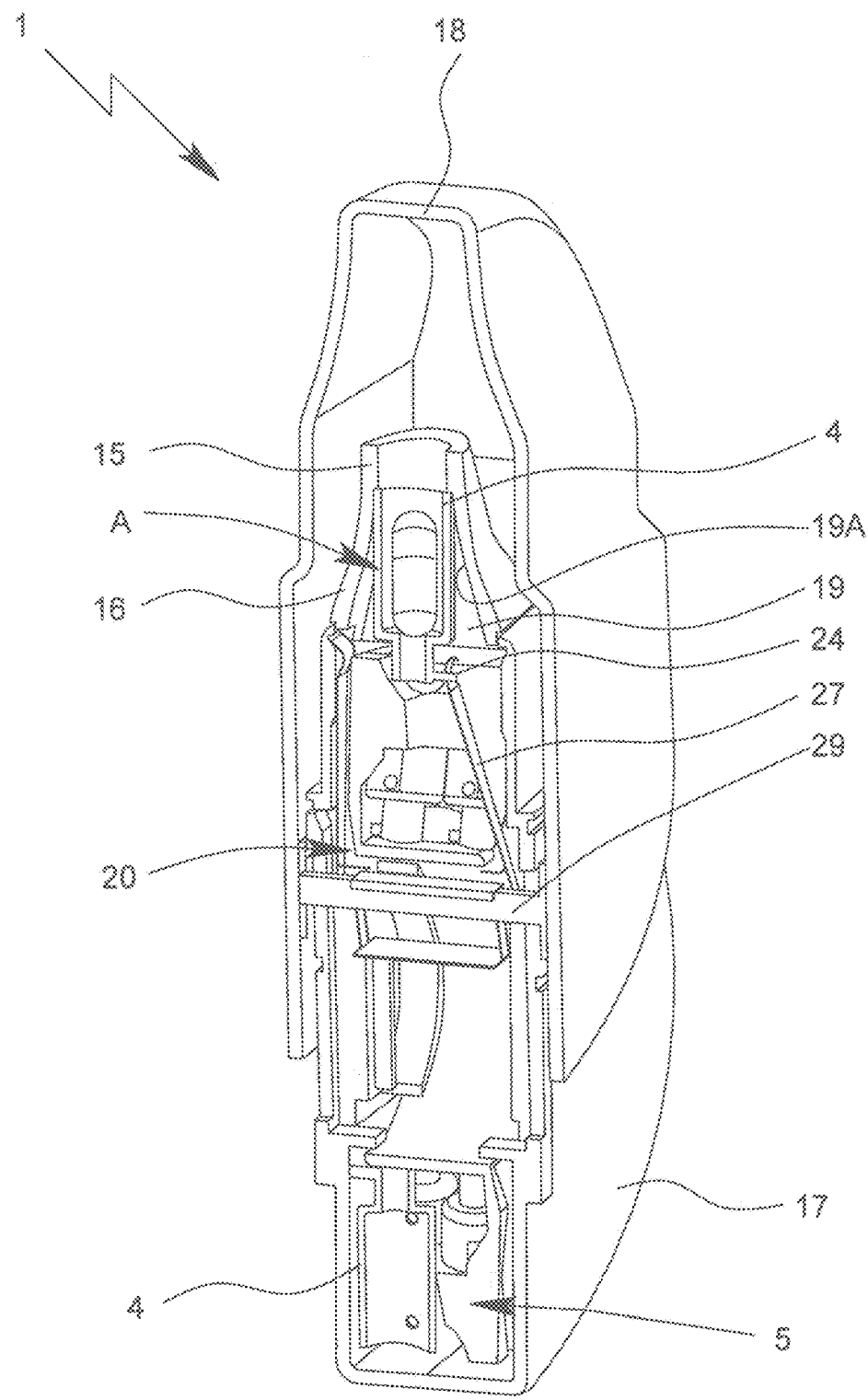
FIG. 24 is a schematic section through the inhaler according to FIG. 21 with the cover completely pulled out radially.

FIG. 24 then shows the corresponding end state when the first opening position is reached, i.e. with the cover 18 completely pulled out radially and with the capsule chamber 4 moved into the discharge position A. In this case, the respective driving element 36 has moved further axially towards the main plane E, in particular by corresponding guiding of the capsule chamber 4 in the receiving chamber 19 and/or by the guide 23 and/or in another manner.

Now the further opening can take place by the cover 18 being pivoted upwards.

After the inhalation and piercing, the cover 18 is closed again. During the radial return movement, the driver 25 is moved back again into its starting position, i.e. into its radially retracted position. In this case, the capsule chamber 4 in engagement with the associated driving element 36 is moved back or retracted again out of the starting position A into the magazine 5.

In the second embodiment, the further rotation of the magazine 5 preferably takes place just before the starting position is reached, i.e. during the radial movement back of the cover 18, wherein the driver 25 or the engagement element 27 thereof has already been decoupled, just beforehand, from the capsule chamber 4 which is moved back into the magazine 5—in particular also by corresponding axial springing out of the engagement element 27. The further rotation of the magazine 5 then takes place by spring force, wherein the release is merely triggered upon reaching the starting position for further rotation about a capsule chamber 4. The spring mechanism (not shown in greater detail) can be realised for example by a watch spring or a leg spring which has sufficient power in order to rotate the magazine 5 in the required manner. Alternatively, a spring mechanism can also be used, which is newly tensioned in each case during opening and/or closing of the cover 18, in particular during pivoting of the cover 18, and in each case relaxes again correspondingly during further rotation of the magazine 5.

In the second embodiment of the inhaler 1, the magazine 5 is preferably configured at least substantially corresponding to the first embodiment, but is adapted to the different configuration of the driver 25, in particular in order to allow the external application in each case of an engagement element 27 to an associated capsule chamber 4 and to guide the other engagement element 27 past on the other side, in each case externally. Furthermore, the capsule chambers 4 with their engagement portions 24 must be directed outwards, in order to allow the required positive engagement with the associated engagement element 27 by engagement in the cutout 28 thereof. This modification constitutes the second embodiment of the proposed magazine 5.

A third embodiment of the proposed inhaler 1 as well as a third embodiment of the proposed magazine 5 are explained in greater detail below with reference to the further drawings.

Figure 25:
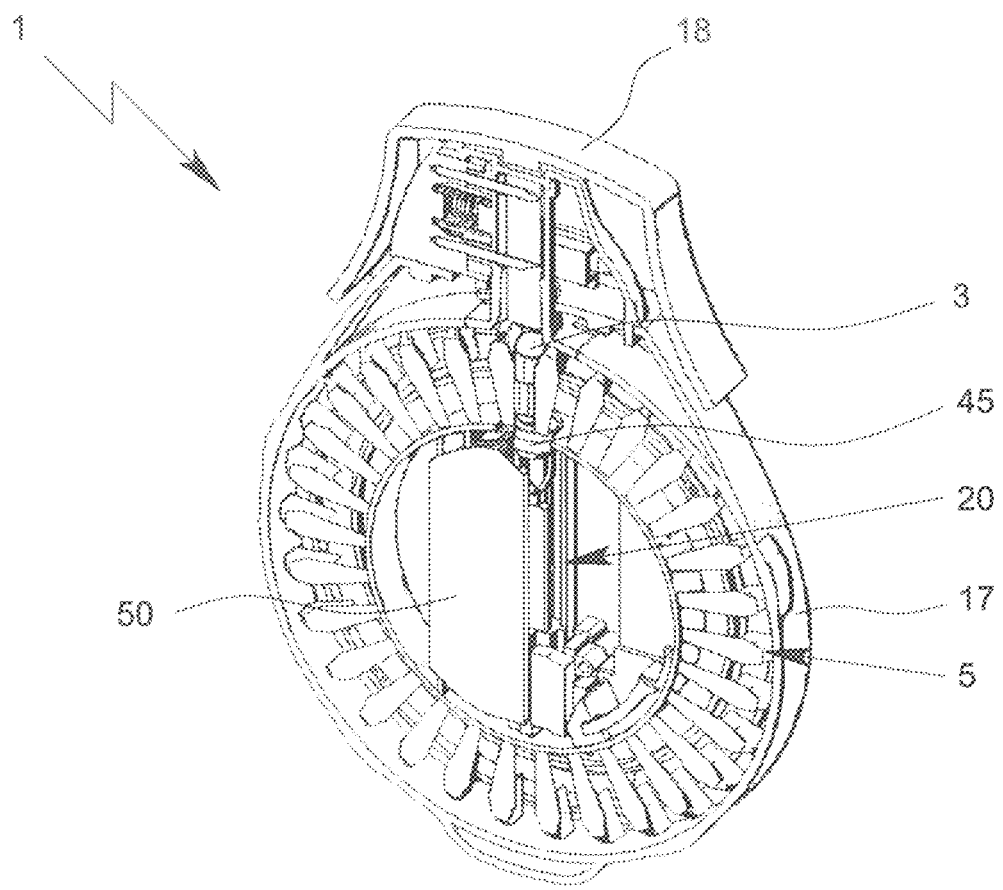
FIG. 25 is a schematic section through a proposed inhaler according to a third embodiment with the cover closed.

FIG. 25 shows the inhaler 1 in a schematic section corresponding to FIG. 5 in the initial state, i.e. with the cover 18 closed. In the third embodiment only the capsules 3, i.e. without capsule chambers 4, can be moved out of the magazine 5 at least substantially radially into the discharge position A or into a receiving chamber 19 or a capsule chamber 4, in order to be opened or pierced there. Accordingly, after the respective capsule 3 is moved in, the common capsule chamber 4 must be closed and opened again for removal of the emptied capsule 3. This preferably takes place with the aid of the (respective) driver 25.

In FIG. 25, for reasons of illustration only one capsule 3 is indicated in the magazine 3, i.e. the support 21 is otherwise not filled.

Figure 26:
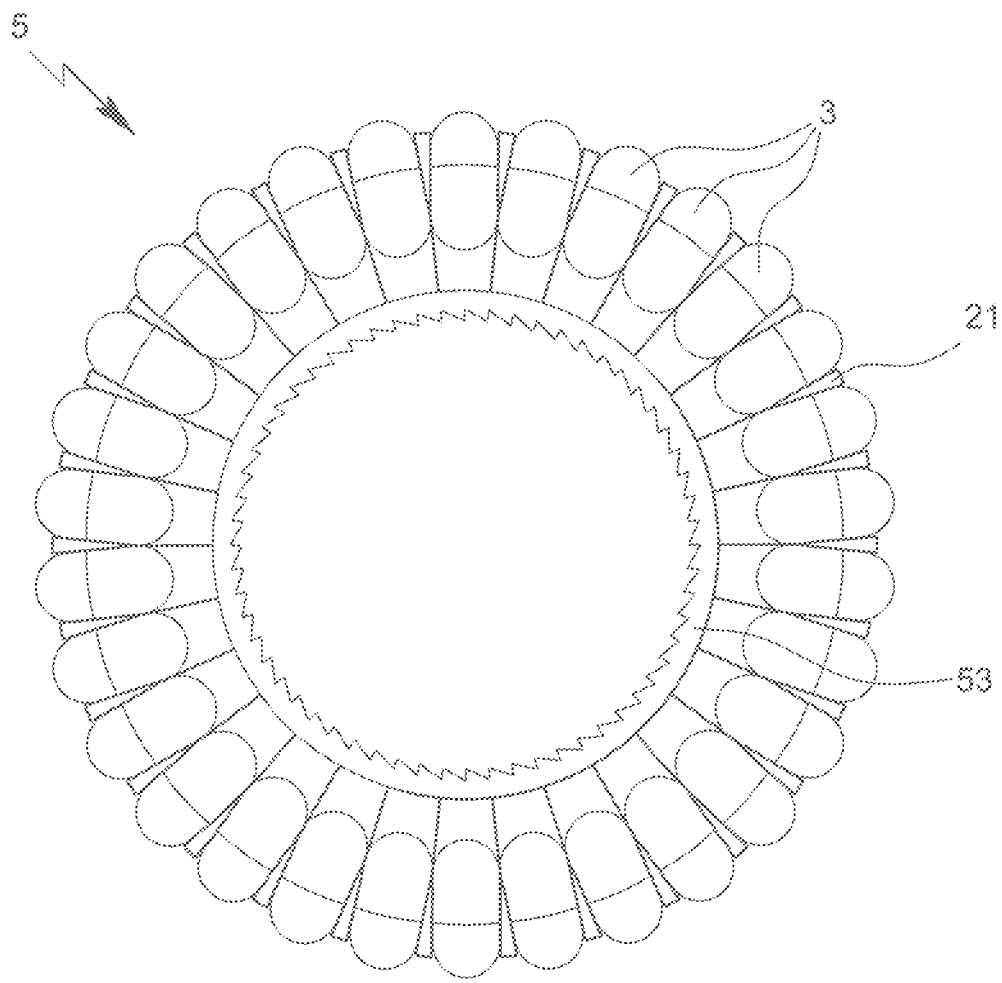
FIG. 26 is a schematic view of a magazine with capsule chambers.

The magazine 5 according to the third embodiment is shown schematically in FIG. 26. Since the magazine 5 contains no capsule chambers 4, it can be more compact or can hold more capsules 3 than is the case when receiving capsules 3 with associated capsule chambers 4. In the example shown, the magazine 5 preferably has 30 capsules 3 in an annular arrangement or plane. The magazine 5 preferably has two annular arrangements of capsules 3 in turn in axially offset planes E1 and E2. In total the magazine 5 preferably has 30 capsules 3 in each annular arrangement or plane E1, E2, 30, i.e. 60 capsules 3 in particular.

The annular arrangements of the capsules 3 are preferably again arranged offset with respect to one another in the circumferential direction, as in the first two embodiments of the magazine 5. Because of the higher number of capsules 3, however, smaller cycle steps or cycle angles are produced during further rotation or forward movement of the magazine 5 to the next capsule 3. In the example shown, in particular for each cycle or each further rotation the rotation angle is only 6° by comparison with the 12° necessary in the first and second embodiment. However, these angles depend upon the number of capsules 3 actually provided in each case as well as the distribution thereof over the circumference of the magazine 5.

The capsules 3 are preferably retained by clamping in the magazine 5 or the support 21 thereof.

Figure 27:
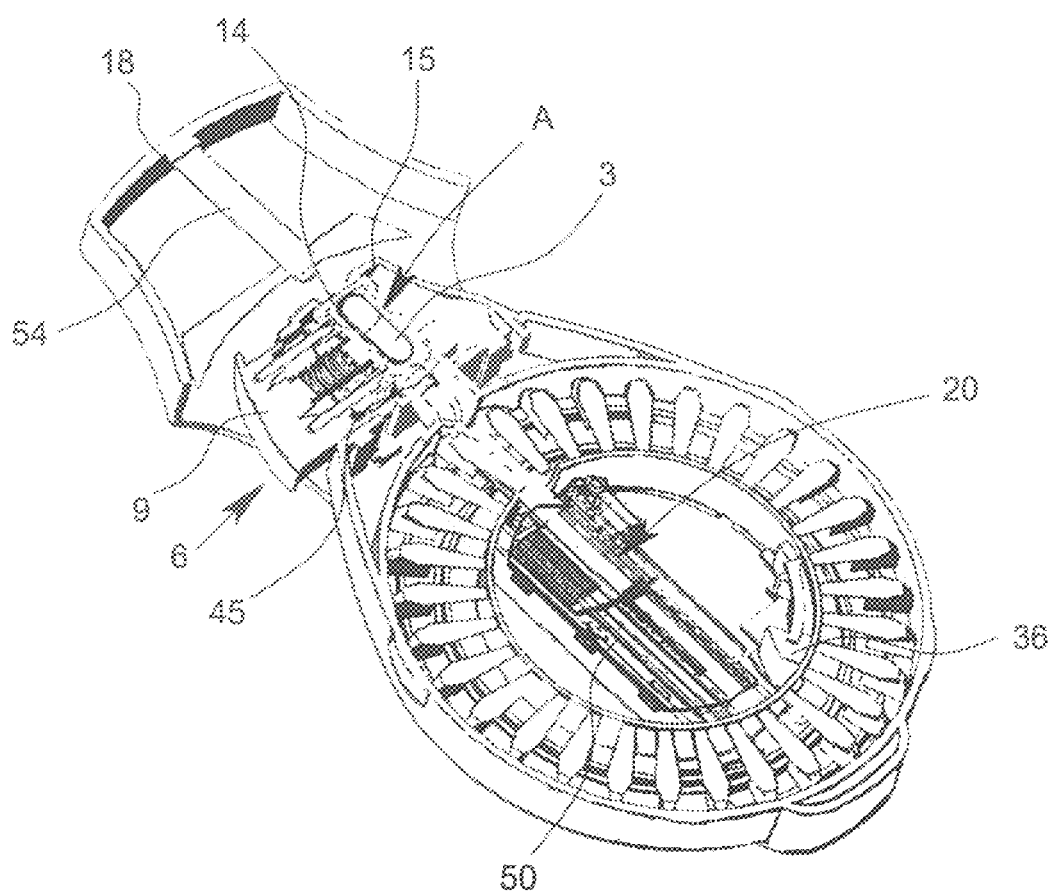
FIG. 27 is a schematic partial section through the inhaler according to FIG. 25 with the cover completely pulled out radially.

FIG. 27 shows the inhaler 1 in a schematic section similar to FIG. 25 but in the first opening state, i.e. with the cover 18 pulled out. The corresponding capsule 3 is located in the discharge position A or in the capsule chamber 4. The capsule chamber 4 which is formed here in the mouthpiece 25 or the connecting portion 16 has been closed on the inlet side by the associated driver 25, preferably however wherein the driver 25 has or forms an inlet 11, so that air can flow into the capsule chamber 4.

Figure 28:
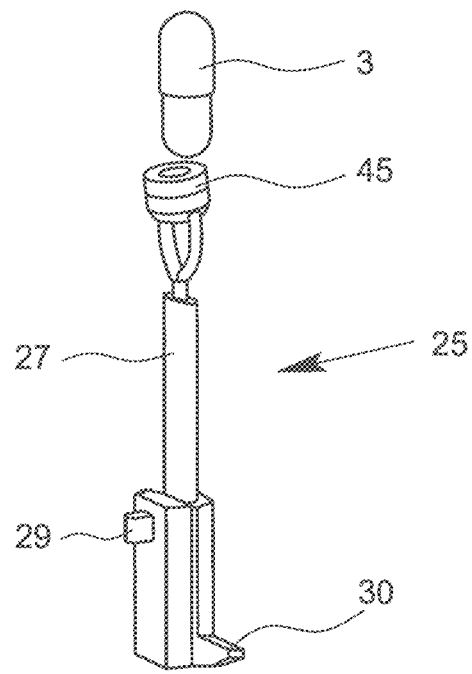
FIG. 28 is a schematic representation of a driver with associated capsule.

FIG. 28 schematically shows a preferred embodiment of the driver 25 with associated capsule 3. In particular, the driver 25 has on its engagement element 27 an adapted, preferably annular, head 45, which closes the capsule chamber 4 and/or forms the inlet 11 thereof, preferably at the base.

Preferably, the driver 25, in particular the head 45, has an opening or hole as the inlet 11. However, other solutions are also possible here.

The head 45 is preferably movable or inclined or inclinable.

The engagement element 27 of the driver 25 can preferably be deflected axially (with respect to the inhaler 1) or transversely, in order to be able to push the capsule 3 located in the main plane E with the head 45 in a defined manner and in particular without tilting into the discharge position A, in particular so that the inlet 11 formed in the head 45 is oriented in a straight line with respect to the longitudinal extent of the capsule chamber 4 or the main discharge direction H.

In the third embodiment, the inhaler 1 or the conveying device 20 thereof preferably has two drivers 25 which are movable independently of one another or alternately for alternating movement in each case of a capsule 3 from one of the annular arrangements or planes E1 or E2 into the discharge position A or into the common capsule chamber 4 and in particular back again into the magazine 5.

For alternating driving of the driver 25, the conveying device 20 preferably has an adjusting slide 46 which, depending upon its axial position, can be brought into engagement selectively with one of the drivers 25.

Figure 29:
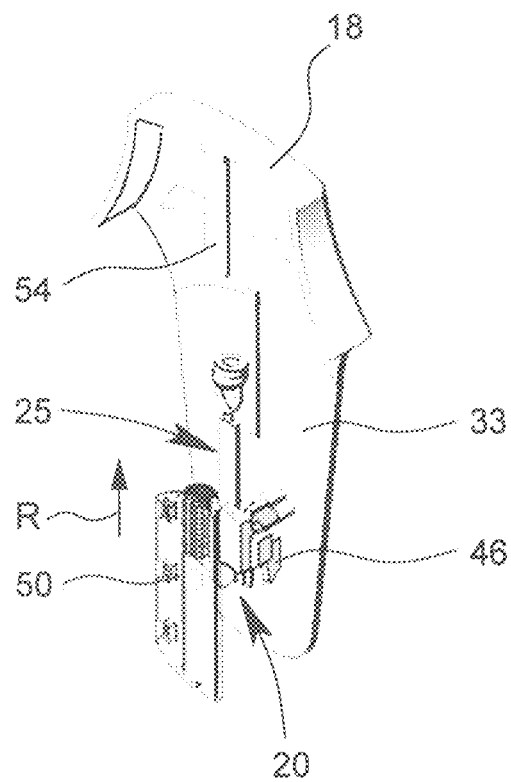
FIG. 29 is a schematic representation of the coupling of a driver with the cover.

The adjusting slide 46 is preferably coupled axially displaceably to the cover 18 or the arms 33 thereof, as indicated schematically in FIG. 29 for one side of the cover 18 and one half of the adjusting slide 46. Thus the adjusting slide 46 extends between the two arms 33 and axially and/or is radially displaceably retained or guided between these arms. Furthermore, the adjusting slide 46 is preferably coupled to the cover 18 or the arms 33 thereof for conjoint rotation with regard to the pivoting movement S.

Figure 30:
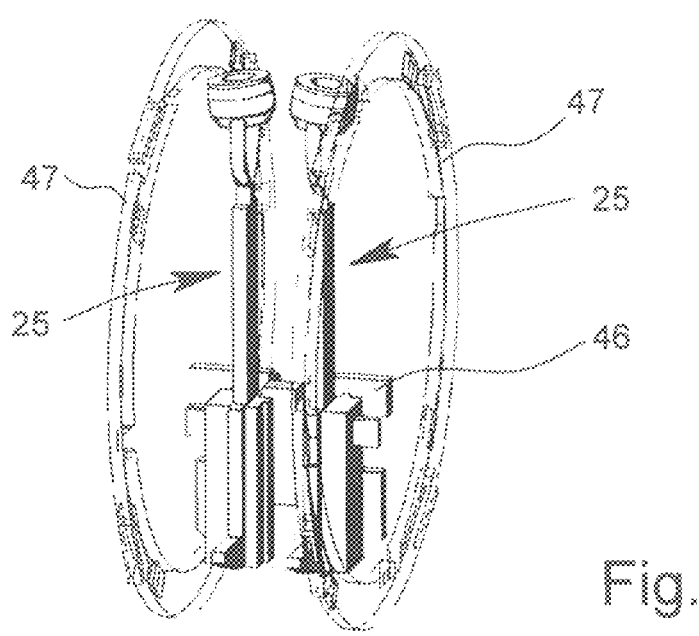
FIG. 30 is a schematic representation of two control rings with associated adjusting slides and drivers.

The inhaler 1 or the conveying device 20 thereof has a switchover device for axial displacement or setting of the axial position of the adjusting slide 46. In the example shown, the switchover device has two control rings 47, which together with the adjusting slide 46 and the associated drivers 25 are indicated schematically in FIG. 30.

Figure 31:
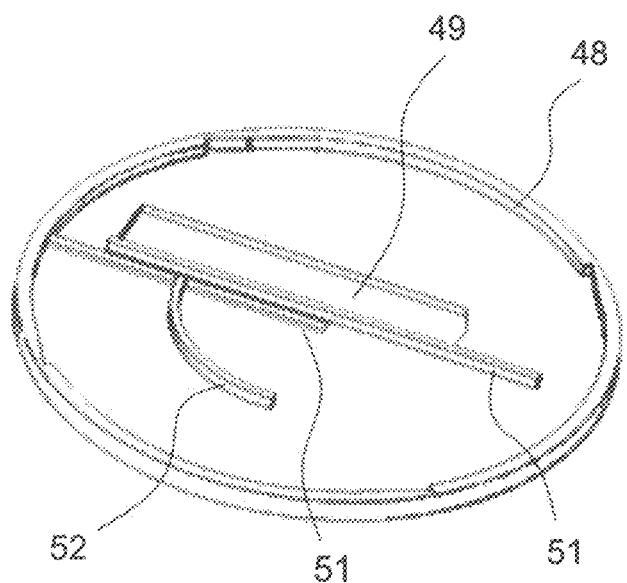
FIG. 31 is a perspective view of a cover.

The inhaler 1 or the housing 17 thereof preferably has on each of its two flat sides a cap 48 which is shown in perspective in FIG. 31. The cap 48 has a movement slot 49 which facilitates the desired coupling or connection of the adjusting slide 46 to the associated arm 33 of the cover 18.

The caps 48 are arranged rotatably on the housing 17 and are coupled for conjoint rotation to the cover 18 or the arms 33 thereof, wherein, however, the radial mobility or displaceability of the cover 18 is maintained.

The control rings 47 are in each case arranged internally on the caps 48 and are driven in rotation thereby in one direction. The control rings 47 are blocked in the other direction, i.e. they freewheel relative to the caps 48. The locking can be implemented in particular by corresponding engagement on the housing 17.

The control rings 47 are always further rotated in steps preferably of 90°, in particular when the cover 18 is in each case pivoted by 90° during opening or closing, as is preferably the case in the examples shown.

The control rings 47 are preferably installed offset by 90° and in each case have control means at the corresponding locations in order to axially displace or move the adjusting slide 46 in the required manner alternately in one and the other direction. This is discussed in greater detail below.

The two drivers 25 are in particular movably guided by means of a guide element 50 inside the magazine 5 in the radial direction R or main discharge direction H, as indicated schematically in FIG. 29 for a driver 25.

Each driver 25 preferably has a spring seat 30 for an associated restoring spring 26, which is supported with its other end in particular by means of a bearing segment 31 on the guide element 50, in order to pretension the respective driver 25 or to move it back into the lower or radially inserted position, as indicated in FIG. 25.

Furthermore, each driver 25 preferably has a further engagement element 29 which in this case is preferably formed as a laterally protruding projection, as indicated in FIG. 28. With this further engagement element 29 the driver 25 engages in a corresponding radial groove 51 in the associated cap 48, which is adjoined by an arcuate groove 52 (cf. FIG. 31), the function of which is considered in greater detail below.

Proceeding from the starting position of the inhaler 1, during opening of the inhaler 1, i.e. with the cover 18 pulled out radially, a corresponding radial movement of the adjusting slide 46 takes place. Depending upon the axial position, the adjusting slide 46 entrains one of the two drivers 25 and pushes it against the force of the associated restoring spring 26 in the radial direction towards the mouthpiece 15, so that this driver 25 pushes the capsule 3 aligned with the mouthpiece 15 out of the magazine 5 at least substantially radially and into the capsule chamber 4 associated with the mouthpiece 15 and closes this by means of the head 45, i.e. it forms an inlet 11 for the capsule chamber 4, such as for example in the representation according to FIG. 1. This state is shown in FIG. 27 and corresponds to the first opening position.

Figure 32:
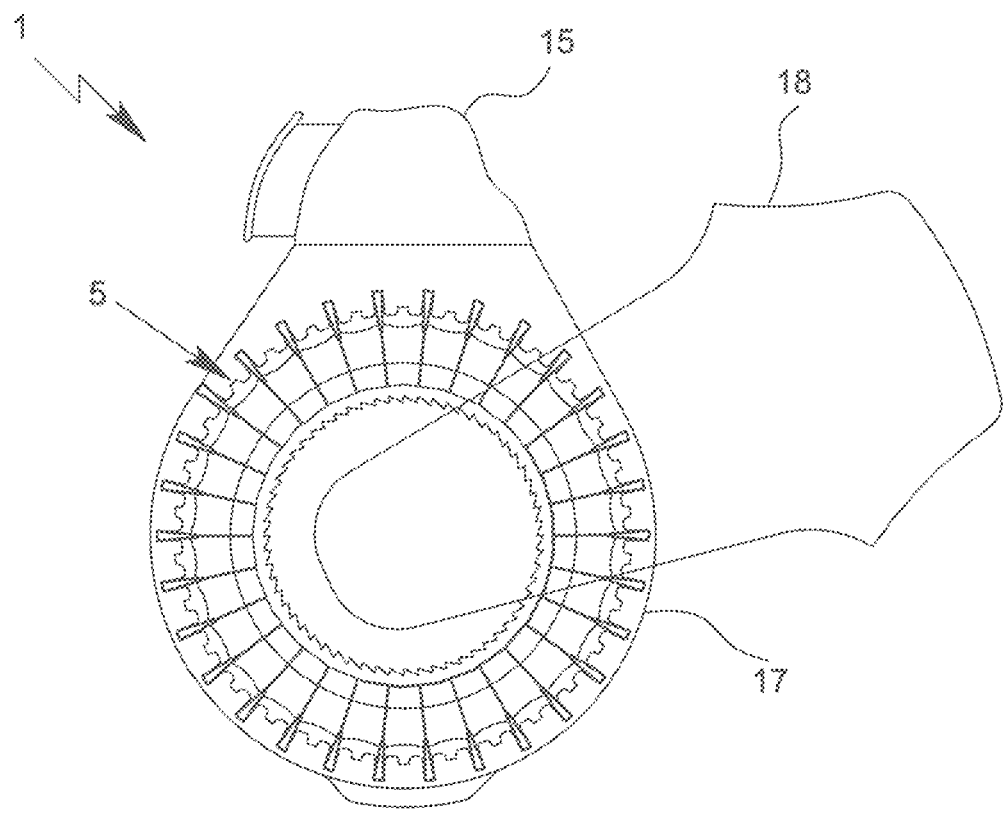
FIG. 32 is a schematic representation of the inhaler according to FIG. 25 with the cover completely pivoted out radially.

Next the cover 18 is pivoted to the side, and the adjusting slide 46 is also moved internally on the magazine 5 or in the circumferential direction. Thus it is no longer possible for the driver 25 which is extended in the radial direction to be held in this radial position by the adjusting slide 46. Thus when the cover 18 is pivoted up, the corresponding cap 48 is also rotated with it, so that the further engagement element 29 engages in the aforementioned arcuate groove 52 of the cap 48, so that the driver 25 with the cover 18 pivoted up is retained or secured in the radially advanced position. FIG. 32 shows such a state with the cover 18 pivoted up.

For driving or rotating the magazine 5, the inhaler 1 has a corresponding driving device. This comprises a driving element 36, as in the first embodiment. In the first embodiment, a driving element 36 is coupled or connected to the cover 18. In the third embodiment, on the other hand, the driving element 36 is independent of the cover 18.

Figure 33:
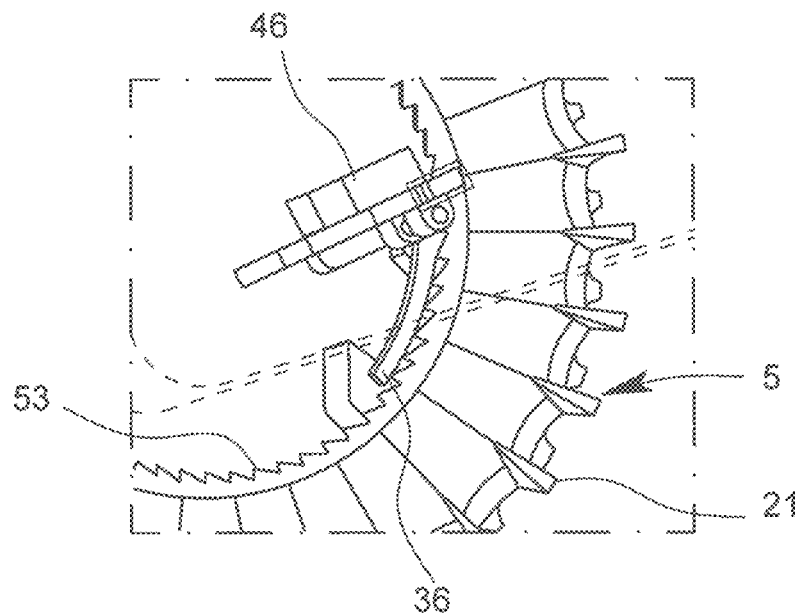
FIG. 33 is a schematic representation of a driving device.

In the third embodiment, the driving element 36 is preferably arranged internally on the magazine 5 and is provided with an external toothing which interacts with an internal toothing 53 on the magazine 5 or the support 21 thereof, as indicated in FIG. 33. In particular, the driving element 36 extends over a certain circumferential region of the internal toothing 53.

Furthermore, the driving element 36 is preferably biased radially outwards, in particular by spring force.

The internal toothing 53 and the corresponding external toothing on the driving element 36 are preferably sawtooth-shaped and/or are configured in such a way that with complete pivoting up of the cover 18 the adjusting slide 46 moved with it comes into abutment in the circumferential direction on the driving element 36 or acts thereon, in order to move the driving element 36 further by one cycle, one catch or one tooth in the circumferential direction relative to the internal toothing 53, in order to prepare for the subsequent further rotation of the magazine 5 by one cycle by a corresponding angular step, in this case preferably of 6°.

Subsequently, the capsule 3 can be opened by actuation of the opening device 6 or of the actuating element 9 and the inhalation can take place.

After the inhalation, the cover 18 is pivoted back again by means of the mouthpiece 15, i.e. back into the first opening position. There are two possible alternatives for this.

When the first opening position is reached, the driver 25 located in the extended radial position or the further engagement element 29 thereof is freed directly and by the force of the associated restoring spring 26 is moved directly back again radially or inwards into the retracted position.

Alternatively, due to the pivoting back the adjusting slide 46 also again comes into contact with the driver 25 located in the extended radial position and therefore is moved, together with the driver 25, by the restoring spring 26 thereof back again into the starting position. During this return movement, the cover 18 is then correspondingly retracted radially into the starting position.

During the radial return movement of the cover 18 into the starting position, i.e. during complete closure of the mouthpiece 15, a spike 54 (cf. FIG. 29) attached internally to the cover 18 is introduced radially into the mouthpiece 15 from the exterior and ensures that the emptied capsule 3 located in the capsule chamber 4 is moved back again into the associated magazine 5, more precisely into the receiving region in the magazine 5 from which the capsule 3 was previously removed. Thus the capsule 3 is in particular pushed back radially again into the magazine 5.

Just before the adjusting slide 46 during the radial return movement again reaches its starting position, a switchover to the other driver 25 and also a further rotation of the magazine 5 preferably take place.

Figure 34:
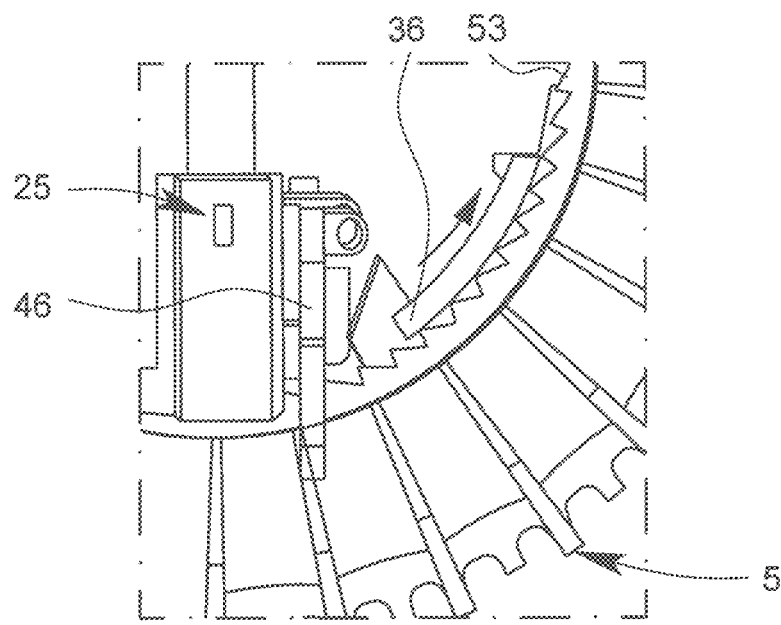
FIG. 34 is a schematic representation of the driving device according to FIG. 33 in the further rotated state of the magazine.

In the example shown, the further rotation of the magazine 5 preferably takes place in that the adjusting slide 46 impinges on a preferably inclined sliding surface of the driving element 36 in order now to move the driving element 36 back again in the opposing circumferential direction into the starting position, wherein due to the engagement of the external toothing of the driving element 36 in the internal toothing of the magazine 5 the required further rotation of the magazine 5 by one capsule 3 or by a required cycle or step of preferably 6° takes place, as indicated in FIG. 34.

It should be noted that other structural solutions are possible. For example, the inclined sliding surface can also be formed if required on the adjusting slide 46 and can slide with a corresponding end of the driving element 36 during the radial movement back of the adjusting slide 46, in order to move the driving element 36 in the required manner in the circumferential direction.

Figure 35:
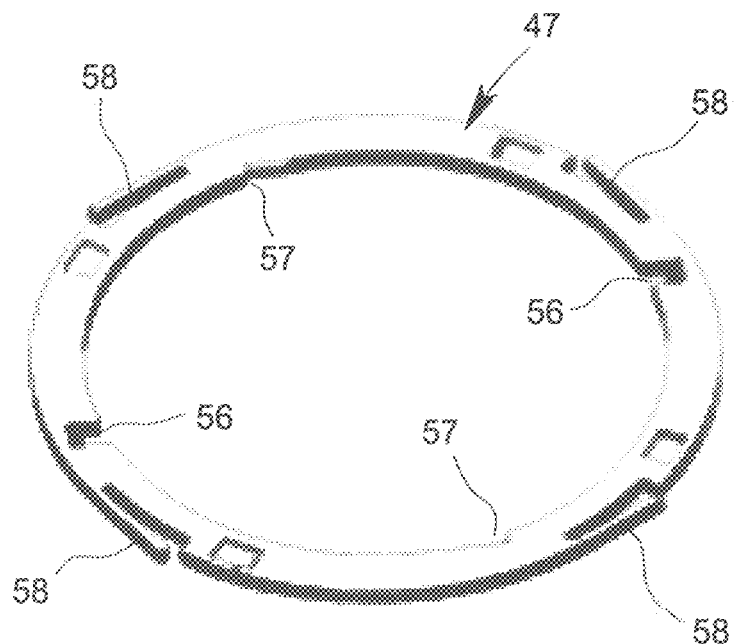
FIG. 35 is a perspective view of a control ring with opposing cutouts and control surfaces.

FIG. 35 is a perspective view of a control ring 47. The control ring 47 preferably has opposing cutouts 56 and opposing control surfaces 57 as control means.

Furthermore, the control ring 47 preferably has one or more locking tabs 58 which in this case are distributed over the circumference in particular in 90° steps. The locking tabs 58 form an anti-reversing lock and ensure that during opening and closing, more precisely during pivoting open and pivoting closed, of the cover 18 and the accompanying rotation of the cap 48 the control ring 47 is in each case further rotated only in one direction, namely in defined steps, in this case in steps of 90°. This defined further rotation leads to the control means successively assuming defined positions and the two control rings 47 also maintaining their position relative to one another. In the example shown, the control rings 47 specifically are preferably installed offset by 90° with respect to one another, so that different control means, i.e. at one time an opposing cutout 56 and a control surface 57 and the next time vice versa, are always located opposite one another.

The locking tabs 58 are preferably arranged on the outer circumference and can co-operate with corresponding latching recesses on the housing 17 in order to produce the rotation lock in one direction.

The control means are preferably arranged on the inner radius of the locking ring 47.

When the adjusting slide 46 is moved back radially into its starting position, i.e. when the cover 18 is closed radially, the adjusting slide 46 just before it reaches its end position impinges on the control surface 57 with an inclined contact surface arranged laterally on a lower end, and due to the inclination according to the principle of the crooked plane transversely with respect to the radial movement, i.e. axially or towards the other control ring 47, where the adjusting slide 46 with its contact surface likewise arranged on the other side can move into the opposing cutout 56. The aforementioned switching over takes place due to this axial movement or transverse displacement. As a result, the adjusting slide 46 is uncoupled from the previous driver 25 and is coupled instead to the other adjusting slide.

When the cover 18 is next opened, the other driver 25 is then accordingly moved radially therewith in the direction of the mouthpiece 15 or towards the discharge position A and accordingly a capsule 3 moves out of the other annular plane of the capsules 3 out of the magazine 5 and into the discharge position A.

In connection with the switching over or the transverse movement or axial movement of the adjusting slide 46, it should be borne in mind that the adjusting slide 46 is retained axially movably between the two arms 33 of the cover 18, in particular by engagement of corresponding lugs, arranged on the arms 33 and projecting axially inwards, in sleeve portions on the adjusting slide 46.

Figure 36:
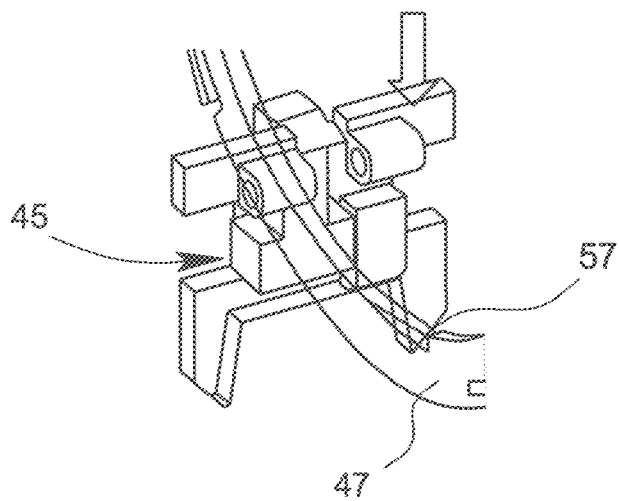
FIG. 36 is a schematic representation of the coupling of the adjusting slide to the control ring.

FIG. 36 shows in a schematic detail the state when the adjusting slide 46 impinges with its contact surface precisely on the control ring 47 or the control surface 57 thereof before, in the further course of the radial movement running downwards in the drawing, the adjusting slide 46 is moved transversely or axially, in this case to the left in order to reach the end position.

The different embodiments of the inhaler 1 and individual features and aspects of the different embodiments can be combined with one another in any way, but can also be implemented independently. The same applies to the magazine 5 and the use of the different embodiments of the magazine 5 in different inhalers 1.

LIST OF REFERENCE SIGNS

| | |
|---|---|
| 1 | inhaler |
| 2 | formulation |
| 3 | capsule |
| 4 | capsule chamber |
| 5 | magazine |
| 6 | opening device |
| 7 | needle |
| 8 | needle opening |
| 9 | actuating element |
| 10 | spring |
| 11 | inlet |
| 12 | outlet |
| 13 | annular shoulder |
| 14 | securing element |
| 15 | mouthpiece |
| 16 | connecting portion |
| 17 | housing |
| 18 | cover |
| 19 | receiving chamber |
| 19A | lead-in chamfer |
| 20 | conveying device |
| 21 | support |
| 22 | retaining portion |
| 23 | guide |
| 24 | engagement portion |
| 25 | driver |
| 26 | restoring spring |
| 27 | engagement element |
| 28 | cutout |
| 29 | further engagement element |
| 30 | spring seat |
| 31 | bearing segment |
| 32 | guide slot |
| 33 | arm |
| 34 | control gate |
| 34A | sector portion |
| 34B | sector portion |
| 34C | annular groove portion |
| 34D | retaining lug |
| 34E | interruption |
| 35 | control element |
| 36 | driving element |
| 37 | guide gate |
| 37A | radial portion |
| 37B | curved portion |
| 38 | drive portion |
| 39 | further cutout |
| 40 | rib which runs forwards |
| 41 | rib which runs backwards |
| 42 | projection |
| 43 | toothed rack |
| 44 | gear |
| 45 | head |
| 46 | adjusting slide |
| 47 | control ring |
| 48 | cap |
| 49 | movement slot |
| 50 | guide element |
| 51 | radial groove |
| 52 | arcuate groove |
| 53 | internal toothing |
| 54 | spike |
| 56 | opposing cutout |
| 57 | control surface |
| 58 | locking tab |
| A | discharge position |
| B | movement |
| D | axis of rotation |
| E | main plane |
| E1 | first capsule plane |
| E2 | second capsule plane |
| E3 | third capsule plane |
| H | main discharge direction |
| R | radial movement |
| S | pivoting movement |

The invention claimed is:

1. An inhaler (1) for the inhalation of a formulation (2) in powder form from a plurality of capsules, where each of the plurality of capsules (3) contain a respective dose of the formulation (2), the inhaler (1) comprising:
a magazine (5) having the plurality of capsules (3), where the magazine is circular, plate-shaped, or disc-shaped, and where the magazine has an axis about which the magazine rotates,
a mouthpiece (15), and
a cover (18) associated with the mouthpiece (15),
wherein the cover (18) is radially movable and pivotable about the axis of the magazine (5) for opening or closing of the mouthpiece (15), by a pivoting (S) of the cover in a first direction, one capsule of the plurality of capsules (3) is moved out of cooperation with the mouthpiece (15) and a next capsule of the plurality of capsules (3) is moved into cooperation with the mouthpiece (15), and by a radial movement (R) of the cover (18) in a radial direction away from the axis, the next capsule of the plurality of capsules (3) is moved in the radial direction relative to the magazine (5), into a discharge position (A), which is a position in which the next capsule of the plurality of capsules (3) is opened and the formulation (2) inhaled by a patient.

2. The inhaler according to claim 1, wherein the magazine (5) further comprises a plurality of capsule chambers (4), and one capsule chamber of the plurality of capsule chambers (4) contains the one capsule of the plurality of capsules (3).

3. The inhaler according to claim 2, wherein the one capsule chamber of the plurality of capsule chambers (4) together with the one capsule of the plurality of capsules (3) is moved out of the magazine (5) into the discharge position (A) by radial movement (R) of the cover (18).

4. The inhaler according to claim 2, wherein the one capsule chamber of the plurality of capsule chambers (4) is radially movably received in the magazine (5) and the one capsule chamber of the plurality of capsule chambers (4) is moved radially into the discharge position (A).

5. The inhaler according to claim 2, wherein the one capsule chamber of the plurality of capsule chambers (4) is movable radially into the discharge position (A).

6. The inhaler according to claim 2, wherein, in order to be conveyed from the one capsule chamber of the plurality of capsule chambers (4) to a next capsule chamber of the plurality of capsule chambers, the magazine (5) is rotatable by the pivoting of the cover (18) in the first direction.

7. The inhaler according to claim 2, wherein, the one capsule of the plurality of capsules (3) or the one capsule chamber of the plurality of capsule chambers (4) is arranged in a radial orientation in a ring with the plurality of capsules or plurality of capsule chambers.

8. The inhaler according to claim 2, wherein, the one capsule of the plurality of capsules (3) or the one capsule chamber of the plurality of capsule chambers (4) is received in the magazine (5) when the cover is moved in the radial movement (R) in the radial direction.

9. The inhaler according to claim 2, wherein the one capsule chamber of the plurality of capsule chambers (4) is moved alternately out of different planes (E1, E2) of the magazine (5) into the discharge position (A) or into a common receiving chamber (19) by means of a lead-in chamfer (19A).

10. The inhaler according to claim 1, wherein, the inhaler (1) further comprises a conveying device (20) for radially conveying at least the one capsule of the plurality of capsules (3) in the radial direction (R) into the discharge position (A), or into the a common receiving chamber (19).

11. The inhaler according to claim 10, wherein the conveying device (20) is arranged inside an annular arrangement formed by the plurality of capsules (3) or is arranged inside the magazine (5).

12. The inhaler according to claim 10, wherein the conveying device (20) has a sliding and/or radially movable driver (25), wherein the driver (25) is radially movable by radial movement (R) of the cover.

13. The inhaler according to claim 10, wherein at least one of the conveying device (20) and driver (25) thereof have two engagement regions or cutouts (28) for alternative or alternating engagement with one capsule of the plurality of capsules (3) in different planes (E1, E2) of the magazine (5).

14. The inhaler according to claim 1, wherein, during closing of the cover (18) or by an uninterrupted pivoting movement of the cover (18) in a second direction for closing the inhaler (1), one capsule of the plurality of capsules (3) located in the discharge position (A) is movable back radially into the magazine (5) and then the magazine (5) is further conveyed or rotated to the next capsule of the plurality of capsules (3) by a positively engaged connection between the cover (18) and the magazine (5).

15. The inhaler according to claim 1, wherein one capsule of the plurality of capsules (3) located in the discharge position (A) is movable back into the magazine (5) by means of spring force.

* * * * *